United States Patent
Yen et al.

(10) Patent No.: US 9,812,649 B2
(45) Date of Patent: Nov. 7, 2017

(54) INDENOTRIPHENYLENE-BASED AMINE DERIVATIVE FOR ORGANIC ELECTROLUMINESCENT DEVICE

(71) Applicant: LUMINESCENCE TECHNOLOGY CORP., Hsin-Chu (TW)

(72) Inventors: Feng-Wen Yen, Taipei (TW); Cheng-Hao Chang, Miao-Li (TW); Chin-Min Teng, Miao-Li (TW)

( * ) Notice: Subject to any disclaimer, the term of this patent is extended or adjusted under 35 U.S.C. 154(b) by 367 days.

(21) Appl. No.: 14/623,508

(22) Filed: Feb. 17, 2015

(65) Prior Publication Data
US 2016/0240783 A1    Aug. 18, 2016

(51) Int. Cl.
| | | |
|---|---|---|
| H01L 51/00 | (2006.01) | |
| C07C 211/61 | (2006.01) | |
| C07D 407/12 | (2006.01) | |
| C07D 209/86 | (2006.01) | |
| C09K 11/06 | (2006.01) | |
| H01L 51/50 | (2006.01) | |

(52) U.S. Cl.
CPC .......... *H01L 51/006* (2013.01); *C07C 211/61* (2013.01); *C07D 209/86* (2013.01); *C07D 407/12* (2013.01); *C09K 11/06* (2013.01); *H01L 51/0056* (2013.01); *H01L 51/0058* (2013.01); *H01L 51/0061* (2013.01); *H01L 51/0072* (2013.01); *H01L 51/0073* (2013.01); *H01L 51/0074* (2013.01); *C09K 2211/1007* (2013.01); *C09K 2211/1029* (2013.01); *H01L 51/0055* (2013.01); *H01L 51/5012* (2013.01); *H01L 51/5056* (2013.01); *H01L 51/5072* (2013.01); *H01L 51/5096* (2013.01)

(58) Field of Classification Search
CPC .. G09G 3/3208; C07D 407/12; C07D 209/86; C09K 2211/1029; C09K 2211/1007; C09K 11/06; H01L 51/5096; H01L 51/5056; H01L 51/0055; H01L 51/5012; H01L 51/0056; H01L 51/0058; H01L 51/0073; H01L 51/0072; H01L 27/3244; H01L 51/0074; H01L 51/006; H01L 51/0061; H01L 51/5072; C07C 13/62; C07C 211/61; H05B 33/14
See application file for complete search history.

(56) References Cited

U.S. PATENT DOCUMENTS

| | | | |
|---|---|---|---|
| 2008/0124572 A1* | 5/2008 | Mizuki | C07C 211/54 428/690 |
| 2013/0048975 A1 | 2/2013 | Hong et al. | |
| 2013/0249968 A1* | 9/2013 | Yamada | C07C 13/62 345/690 |
| 2014/0131664 A1 | 5/2014 | Yen et al. | |
| 2014/0151645 A1 | 6/2014 | Yen et al. | |
| 2014/0166988 A1 | 6/2014 | Yen et al. | |
| 2014/0175384 A1 | 6/2014 | Yen et al. | |
| 2014/0209866 A1 | 7/2014 | Yen et al. | |
| 2014/0231754 A1 | 8/2014 | Yen et al. | |

FOREIGN PATENT DOCUMENTS

| | | | | |
|---|---|---|---|---|
| WO | 2008062636 A1 | | 5/2008 | |
| WO | WO 2008062636 | * | 5/2008 | ............. H01L 51/50 |
| WO | 2012091471 A2 | | 7/2012 | |
| WO | WO 2012091471 | * | 7/2012 | ........... C07C 211/54 |

* cited by examiner

Primary Examiner — Alexander Kollias

(57) ABSTRACT

The present invention discloses an indenotriphenylene-based amine derivative represented by the following formula (A):

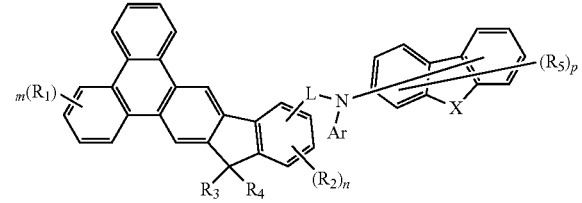

formula (A)

wherein $R_1$ to $R_5$, m, n, p, L and Ar are the same definition as described in the present invention. The present invention also discloses an organic EL device employing the indeno-triphenylene-based amine derivative as a hole transport material or an electron blocking material, which can lower driving voltage and power consumption and increase efficiency and half-life time.

7 Claims, 1 Drawing Sheet

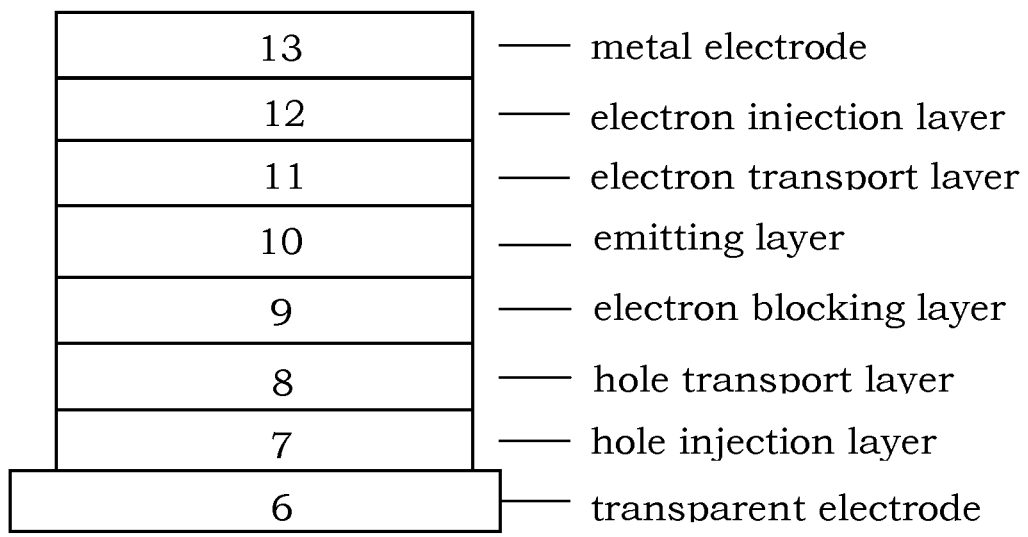

INDENOTRIPHENYLENE-BASED AMINE DERIVATIVE FOR ORGANIC ELECTROLUMINESCENT DEVICE

FIELD OF INVENTION

The present invention generally relates to a indenotriphenylene-based amine derivative and organic electroluminescent (herein referred to as organic EL) device using the derivative. More specifically, the present invention relates to the derivative having general formula (A), an organic EL device employing the derivative as hole transport material, electron blocking material.

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden. Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC).

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

There continues to be a need for organic EL materials which is able to efficiently transport electrons or holes and block electrons or holes, with good thermal stability, and more efficient hole transport material (HTM) and electron blocking material (EBM) that can lower driving voltage and power consumption, increasing efficiency and half-life time. According to the reasons described above, the present invention has the objective of resolving such problems of the prior-art like as EP2313362A1, US20130048975A1, WO20080672636A1, WO2012091471A2. In the present invention we used diarylamine group linked to the indenotriphenylene core and offering a light emitting device which is excellent in its thermal stability, high luminance efficiency, high luminance and long half-life time to improve the prior materials and the prior organic EL device.

SUMMARY OF THE INVENTION

Provided a indenotriphenylene-based amine derivative can use as hole transport material, electron blocking material for organic EL device. The compound can overcome the drawbacks of the prior materials such as EP2313362A1, US20130048975A1, WO20080672636A1, WO2012091471A2, like as lower efficiency, half-lifetime and higher power consumption.

An object of the present invention is to provide the indenotriphenylene-based amine derivative which can be used as hole transport layer, electron blocking layer for organic EL device.

The present invention has the economic advantages for industrial practice. Accordingly the present invention, the indenotriphenylene-based amine derivative which can be used as hole transport material, electron blocking material for organic EL device is disclosed. The mentioned the indenotriphenylene-based amine derivative is represented by the following formula (A):

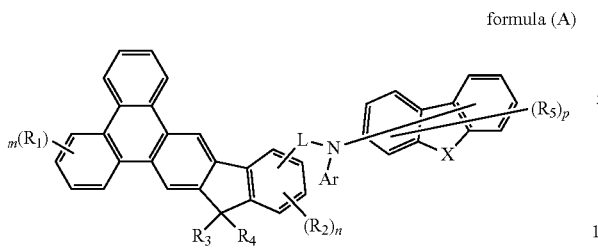

formula (A)

wherein L represents a single bond, a substituted or unsubstituted divalent arylene group having 6 to 30 carbon atoms; m represents an integer of 0 to 10; n represents an integer of 0 to 3; p represents an integer of 0 to 7; X is absent or represents a divalent bridge selected from the atom or group consisting from O, S, $C(R_6)(R_7)$, and $NR_8$; $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms, and a substituted or unsubstituted heteroaryl group having 3 to 30 carbon atoms; Ar is selected from the group consisting of a substituted or unsubstituted aryl group having 6 to 50 carbon atoms, and a substituted or unsubstituted heteroaryl group having 3 to 50 carbon atoms.

BRIEF DESCRIPTION OF THE DRAWINGS

FIG. 1 show one example of organic EL device in the present invention. 6 is transparent electrode, 13 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is electron transport layer which is deposited onto 10, 12 is electron injection layer which is deposited on to 11.

DESCRIPTION OF THE PREFERRED EMBODIMENTS

What probed into the invention is the indenotriphenylene-based amine derivative and organic EL device using the indenotriphenylene-based amine derivative. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the indenotriphenylene-based amine derivative which can be used as hole transport material, electron blocking material for organic EL device are disclosed. The mentioned derivative is represented by the following formula (A):

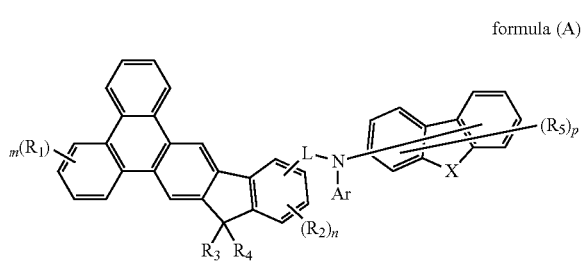

formula (A)

wherein L represents a single bond, a substituted or unsubstituted divalent arylene group having 6 to 30 carbon atoms; m represents an integer of 0 to 10; n represents an integer of 0 to 3; p represents an integer of 0 to 7; X is absent or represents a divalent bridge selected from the atom or group consisting from O, S, $C(R_6)(R_7)$, and $NR_8$; $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms, and a substituted or unsubstituted heteroaryl group having 3 to 30 carbon atoms; Ar is selected from the group consisting of a substituted or unsubstituted aryl group having 6 to 50 carbon atoms, and a substituted or unsubstituted heteroaryl group having 3 to 50 carbon atoms.

According to the above-mentioned formula (A) wherein L is represented the following:

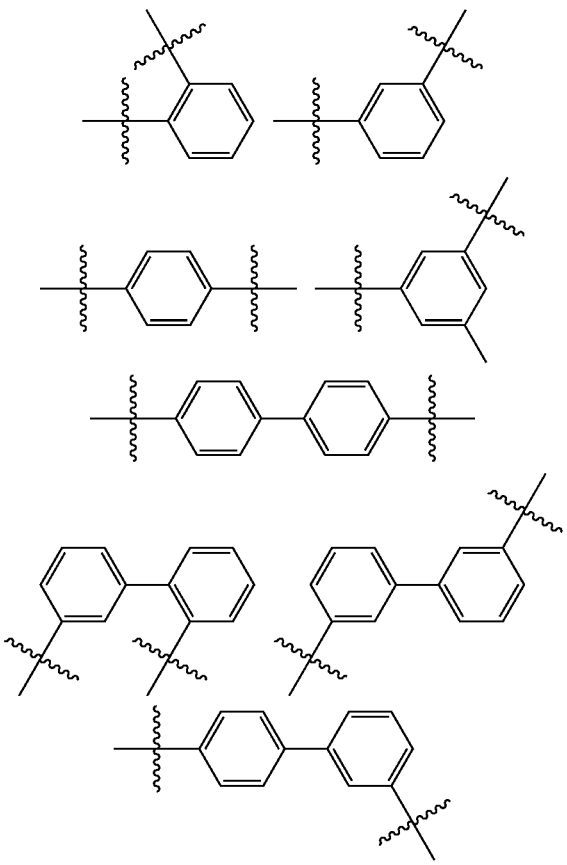

According to the above-mentioned formula (A) wherein Ar is represented the following:
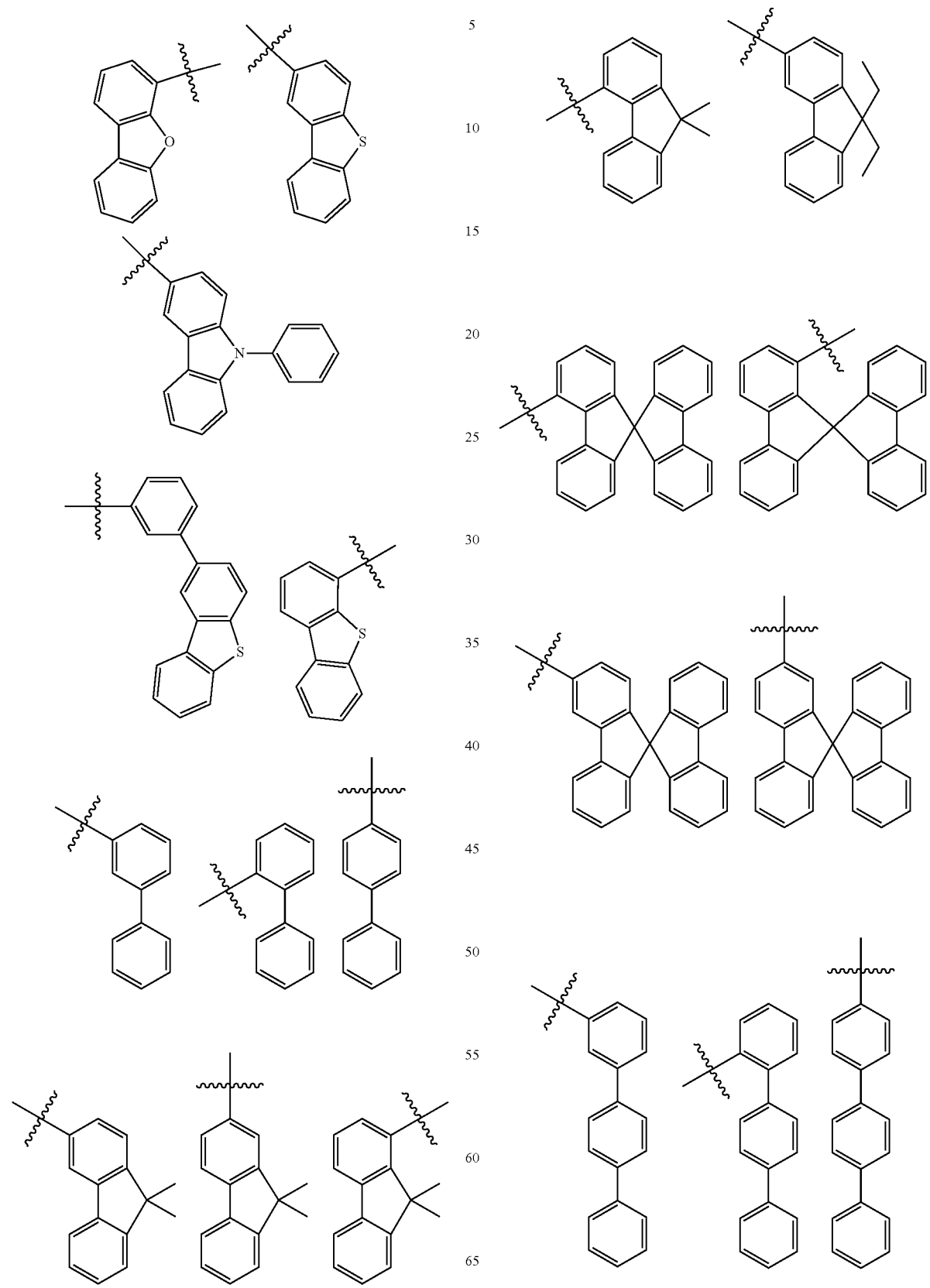

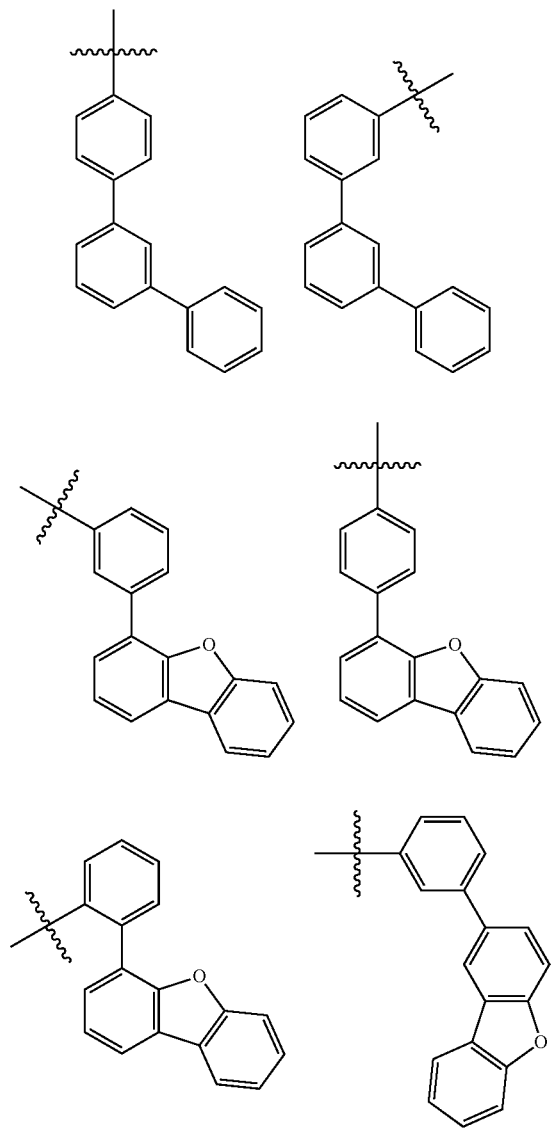
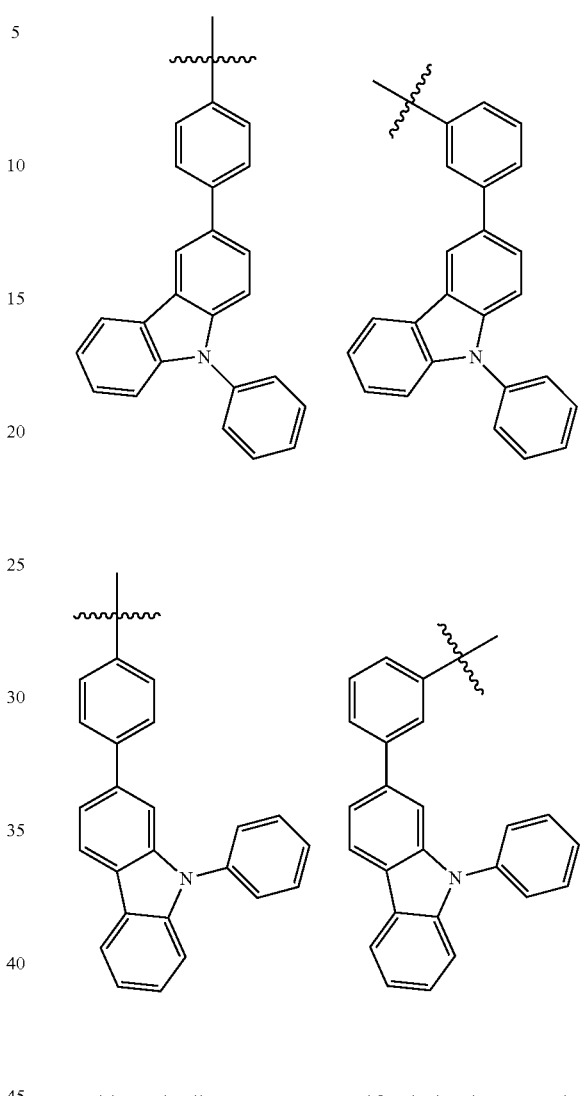
In this embodiment, some specific derivatives are shown below:
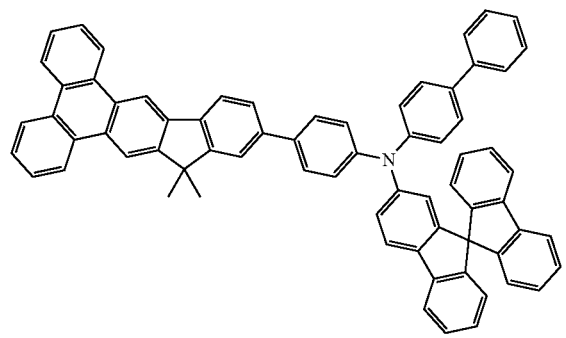
A1
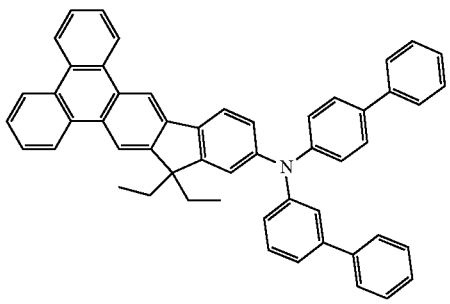
A2

A3
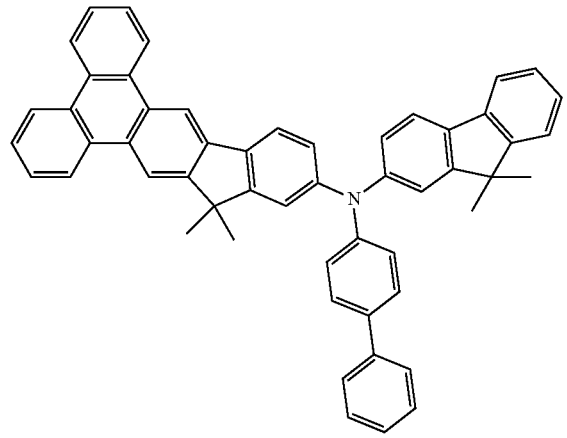
A4
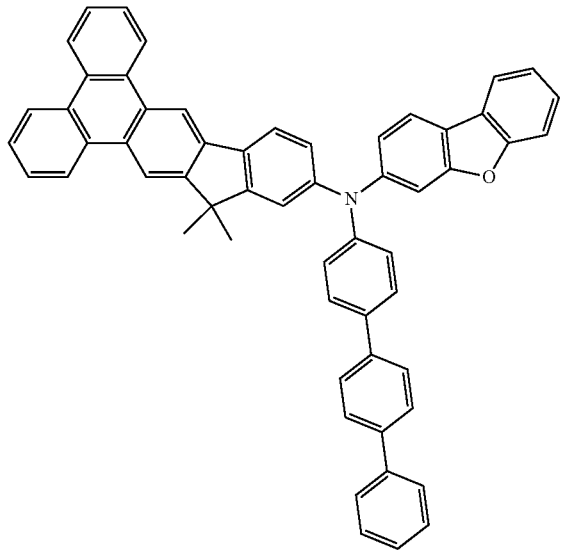
A5
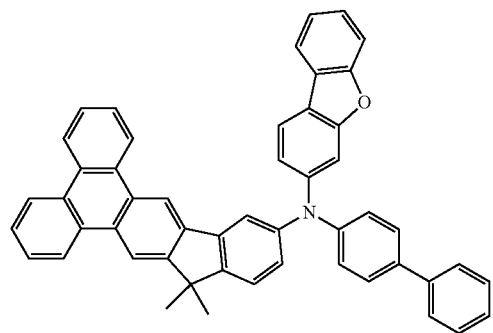
A6
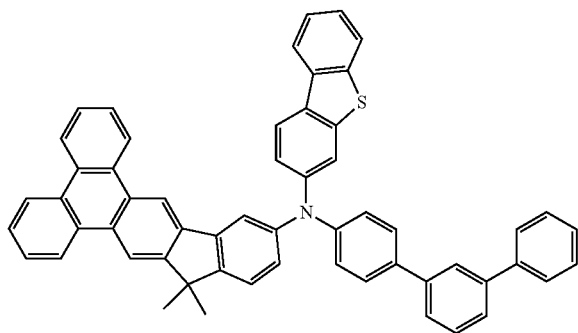
A7
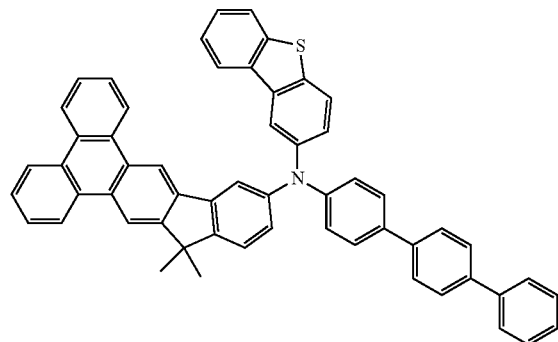
A8
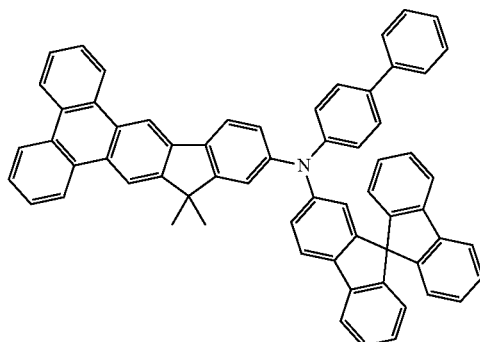

-continued
A9
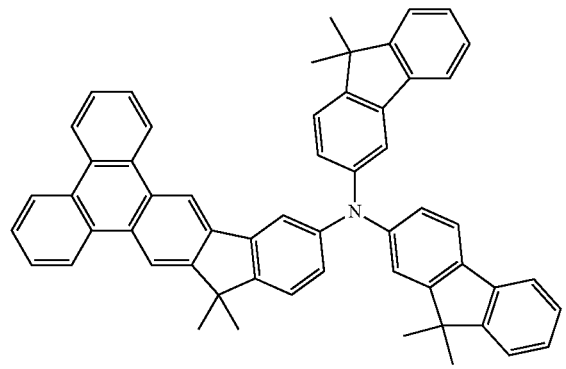
A10
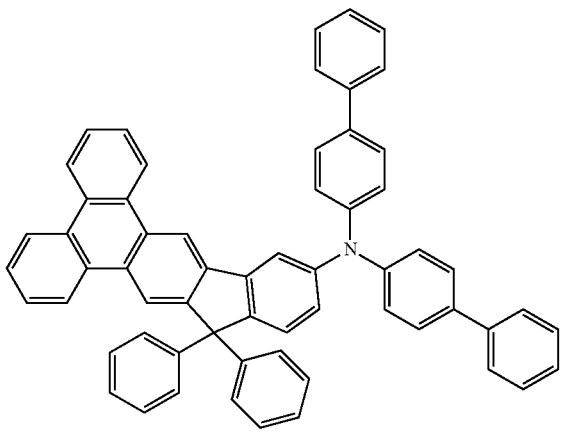
A11
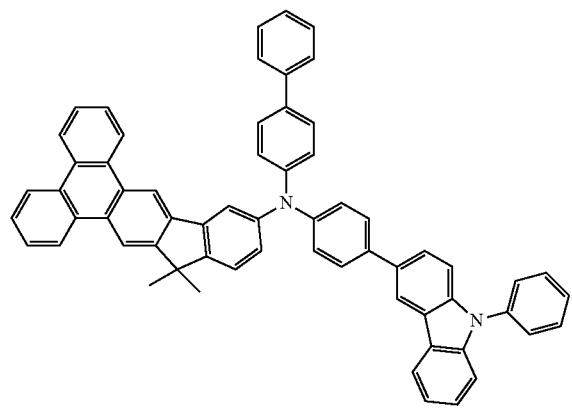
A12
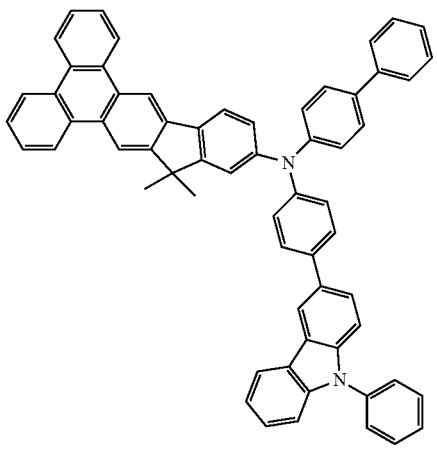
A13
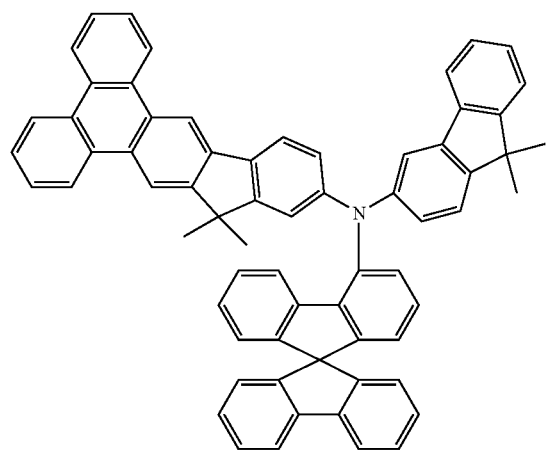
A14
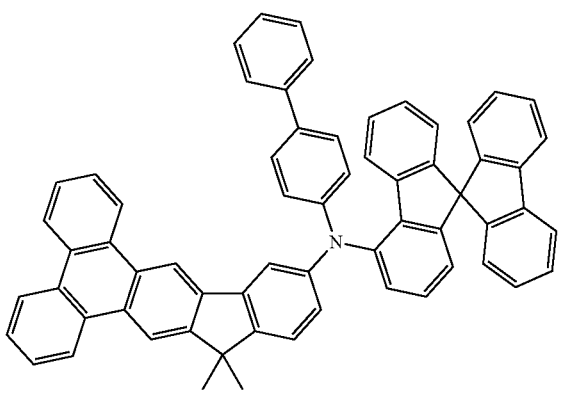

-continued
A15
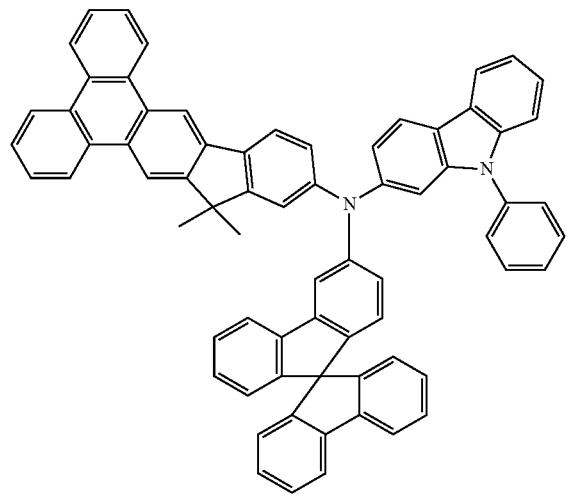
A16
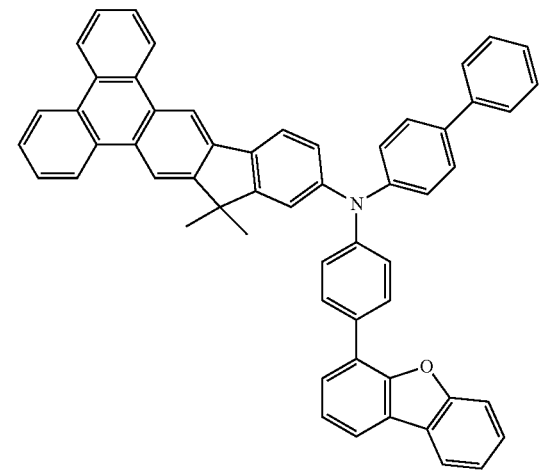
A17
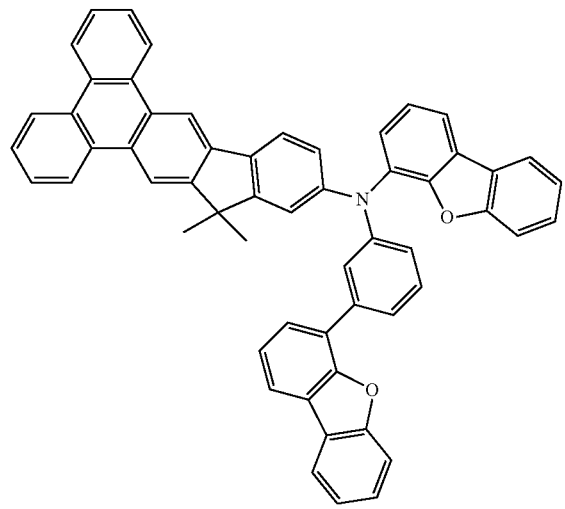
A18
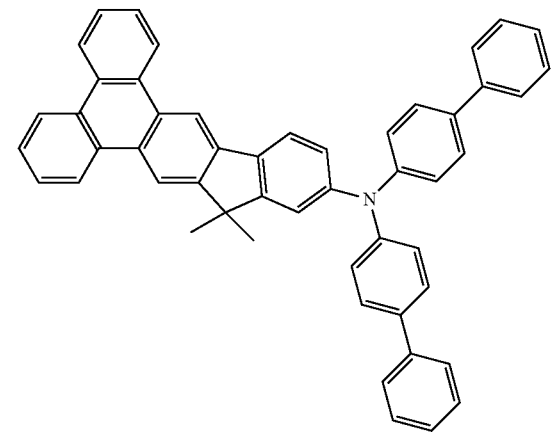
A19
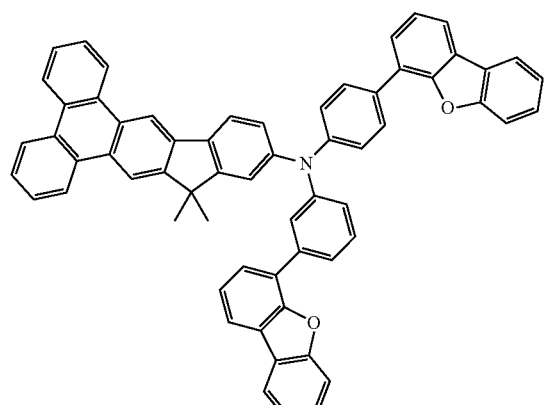
A20
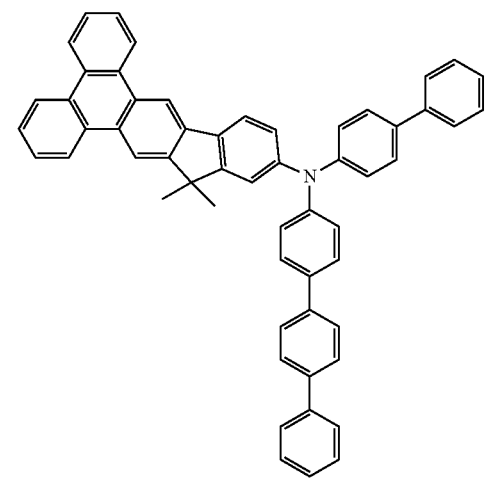

-continued
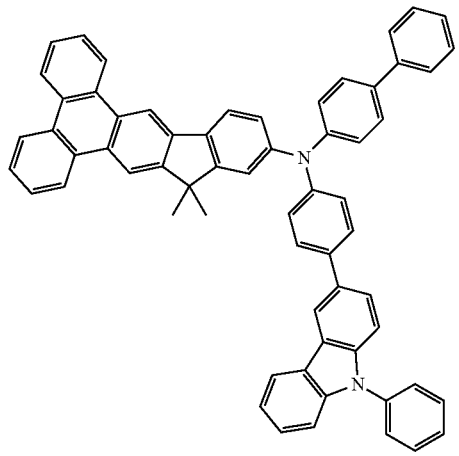
A21
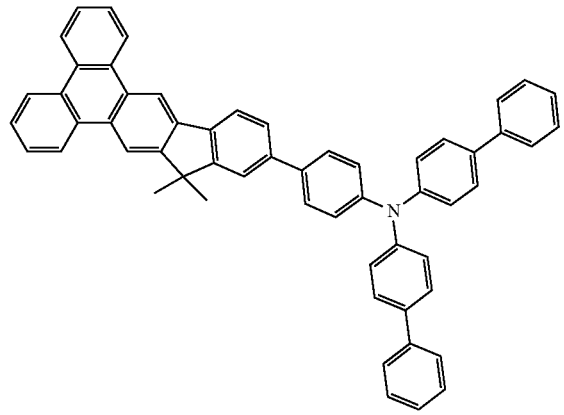
A22
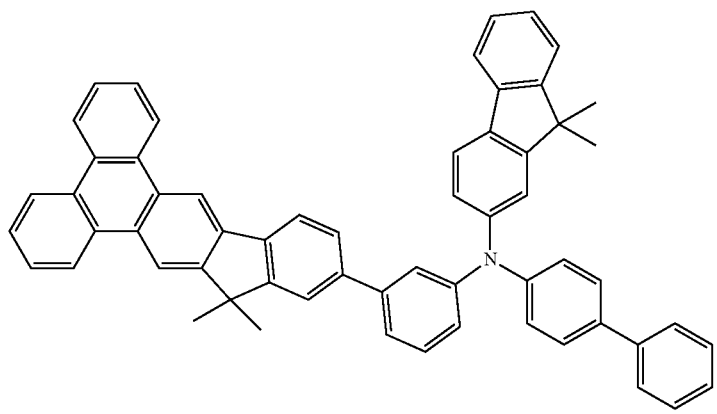
A23
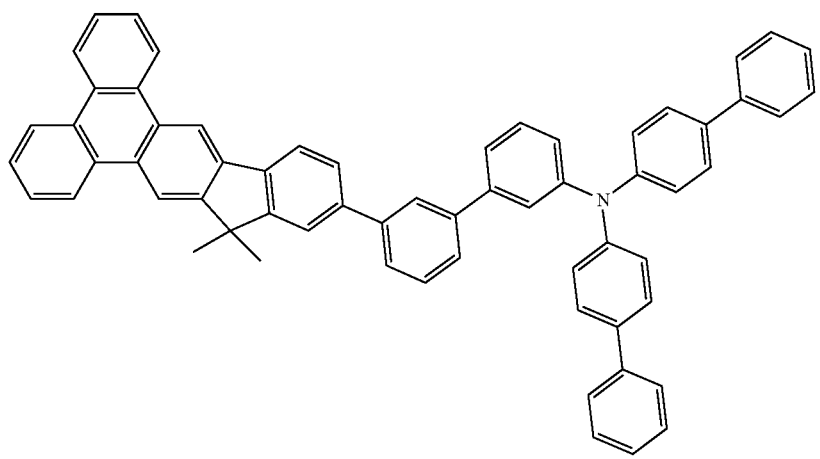
A24

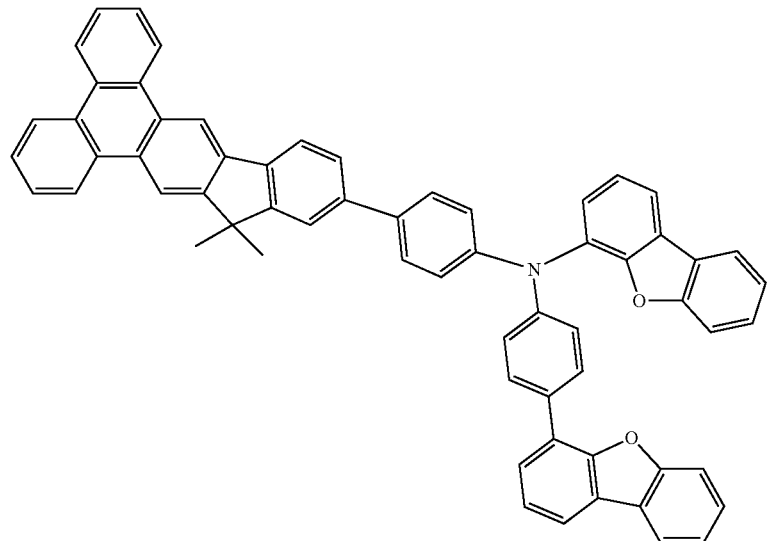
A25
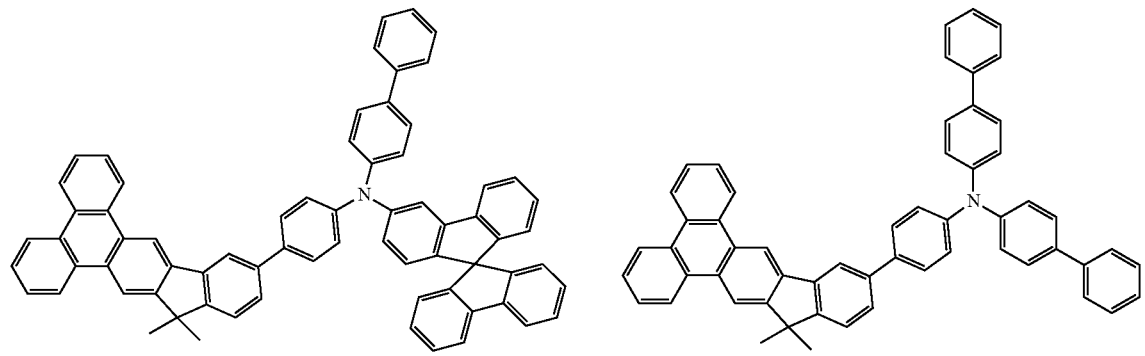
A26  A27
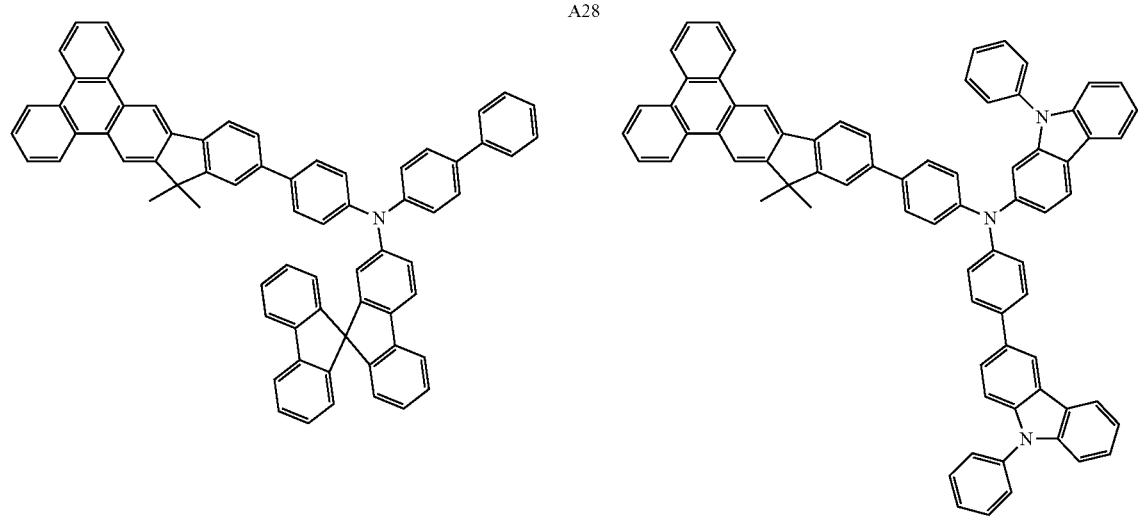
A28  A29

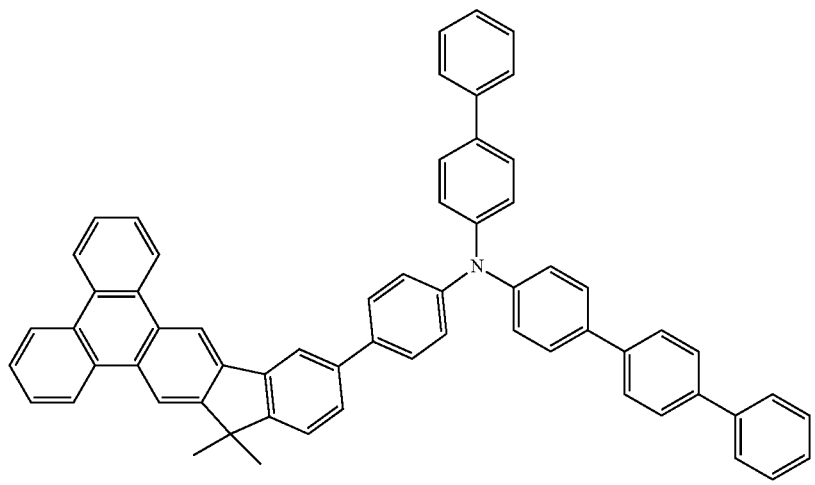

A30

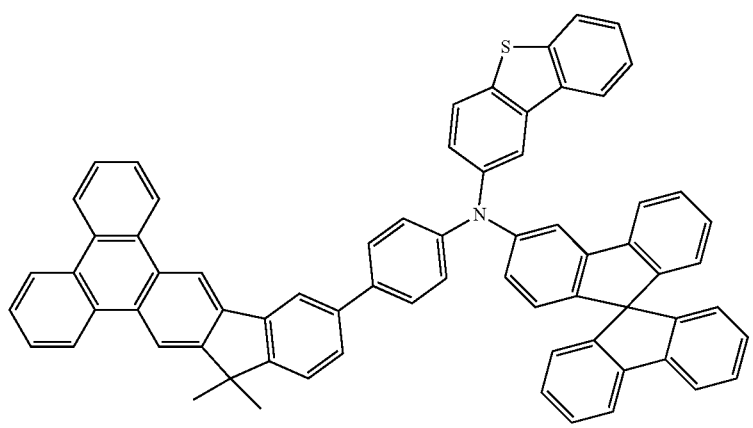

A31

Detailed preparation for the indenotriphenylene-based amine derivative in the present invention could be clarified by exemplary embodiments, but the present invention is not limited to exemplary embodiments. EXAMPLE 1~6 show the preparation for some EXAMPLES of the derivative in the present invention. EXAMPLE 7~8 show the fabrication of organic EL device and I-V-B, half-life time of organic EL device testing report.

EXAMPLE 1

Synthesis of Derivative A1

Synthesis of 2-(biphenyl-2-yl)-7-bromo-9,9-dimethyl-9H-fluorene

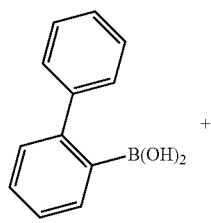

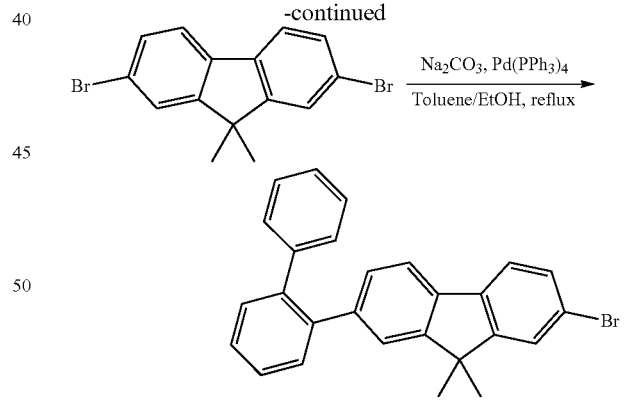

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of Pd(PPh$_3$)$_4$, 75 ml of 2M Na2CO3, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of 12-bromo-10,10-dimethyl-10H-indeno[2,1-b]triphenylene

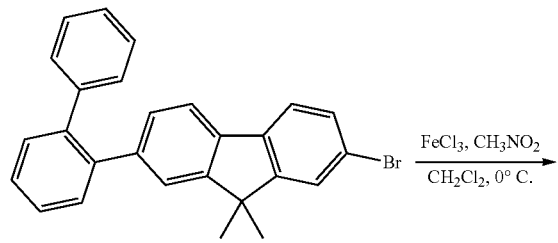

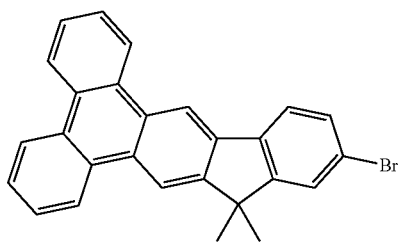

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron(III)chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). $^1$H NMR (CDCl3, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of N-(biphenyl-4-yl)-9,9'-spirobifluorene-2-amine

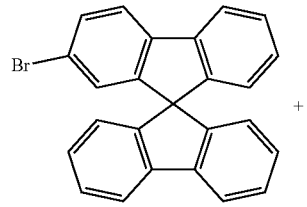

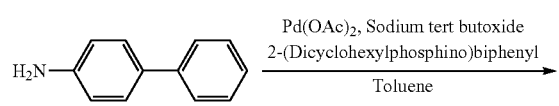

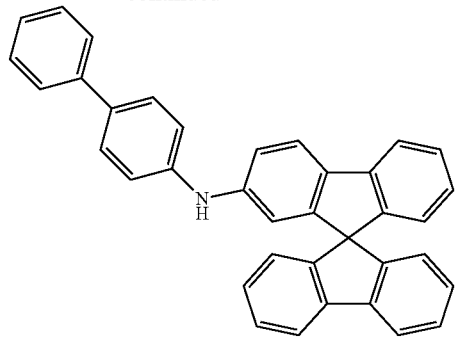

A mixture of 30 g (75.8 mmol) 2-bromo-9,9'-spirobifluorene, 15.3 g (90.9 mmol) of biphenyl-4-amine, 0.17 g (0.76 mmol) of palladium(II) acetate, 0.26 g (0.76 mmol) of 2-(dicyclohexylphosphino)biphenyl, 9.5 g (98.5 mmol) of sodium tert-butoxide and 300 ml of toluene was refluxed under nitrogen overnight. After finishing the reaction, than cooled to room temperature. The organic layer was extracted with dichloromethane and water, dried with anhydrous magnesium sulfate, the solvent was removed and the residue was purified by column chromatography on silica(hexane-dichloromethane) to give product 21.9 g (yield 60%) as a white solid.

Synthesis of N-(biphenyl-4-yl)-N-(4-bromophenyl)-9,9'-spirobifluorene-2-amine

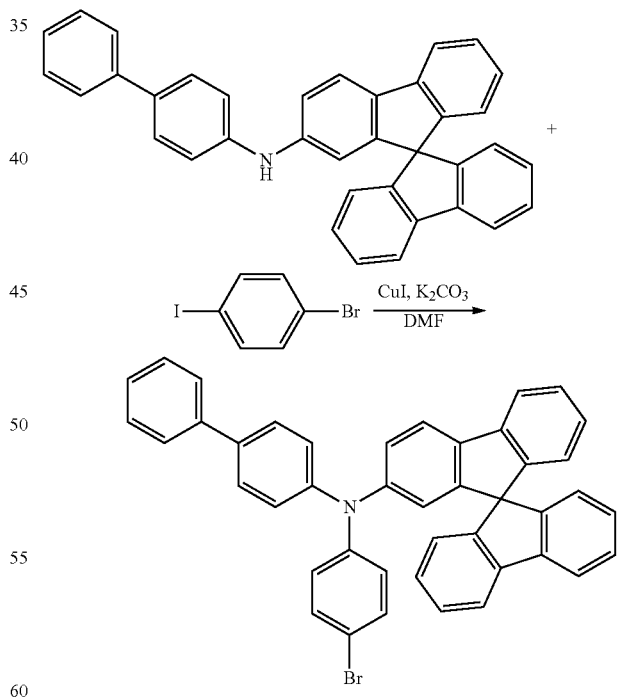

A mixture of 20 g (41.3 mmol) N-(biphenyl-4-yl)-9,9'-spiro bifluorene-2-amine, 14 g (49.5 mmol) of 1-bromo-4-iodobenzene, 2.4 g (12.4 mmol) of copper iodide, 17.1 g (123.9 mmol) of potassium carbonate and 300 ml of DMF was refluxed under nitrogen overnight. After finishing the reaction, than cooled to room temperature. The organic layer was extracted with ethyl acetate and water, dried with anhydrous magnesium sulfate, the solvent was removed and the residue was purified by column chromatography on silica (hexane-dichloromethane) to give product 26.3 g (yield 43%) as a white solid.

Synthesis of intermediate of N-(biphenyl-4-yl)-N-(4-(4,4,5,5-tetramethyl-1,3,2-dioxaborolan-2-yl)phenyl)-9,9'-spirobi[fluoren]-2-amine

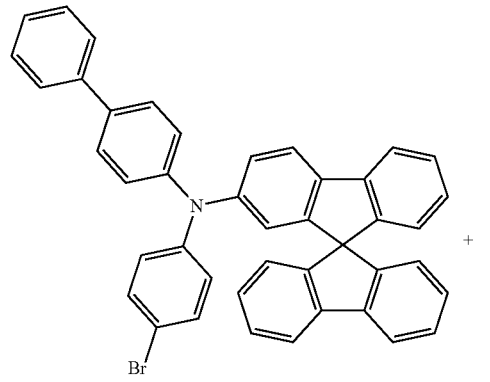

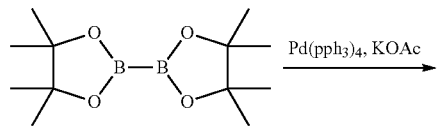

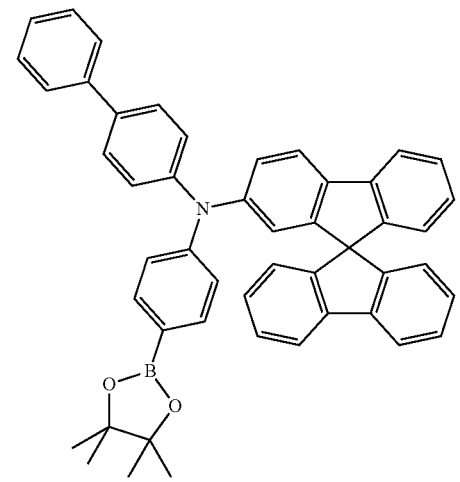

A mixture of 10 g (15.6 mmol) of N-(biphenyl-4-yl)-N-(4-bromophenyl)-9,9'-spirobi[fluoren]-2-amine, 4.75 g (18.72 mmol) of bis(pinacolato)diboron, 0.18 g (0.156 mmol) of tetrakis(triphenylphosphine)palladium, 2 g (20.28 mmol) of potassium acetate, and 300 ml of 1,4-dioxane was degassed and placed under nitrogen, and then heated at 90° C. for 16 h. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl as eluent to get 8.77 g of light yellow product (yield 82%).

Synthesis of N-(biphenyl-4-yl)-N-(4-(10,10-dimethyl-10H-indeno[1,2-b]triphenylen-12-yl)phenyl)-9,9'-spirobi[fluoren]-2-amine

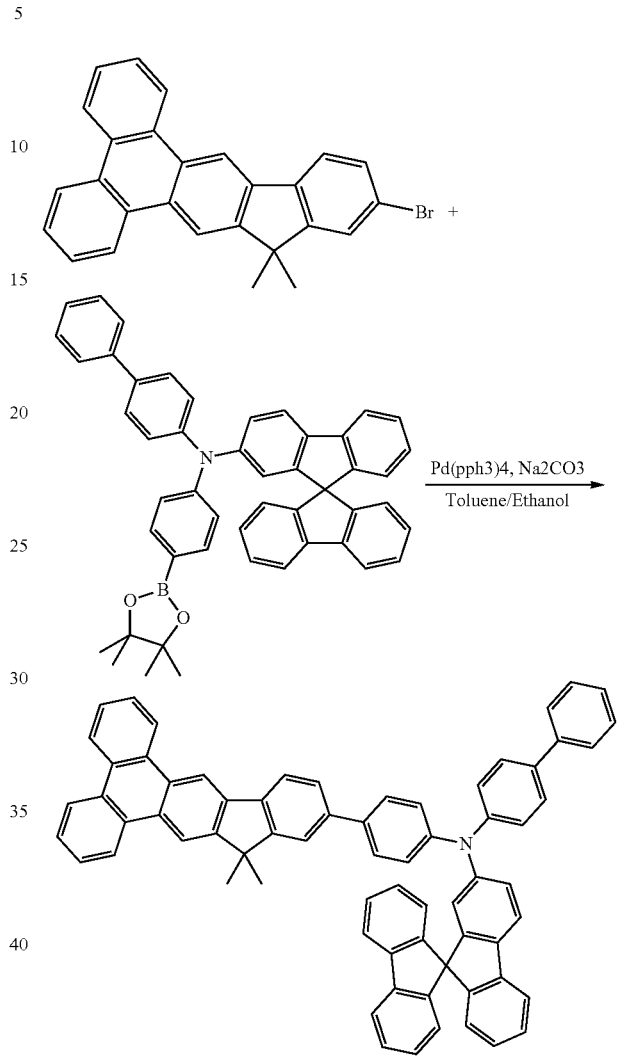

A mixture of 15 g (35.43 mmol) of 12-bromo-10,10-dimethyl-10H-indeno[1,2-b]triphenylene, 29.1 g (42.51 mmol) of N-(biphenyl-4-yl)-N-(4-(4,4,5,5-tetramethyl-1,3,2-dioxaborolan-2-yl)phenyl)-9,9'-spirobifluorene-2-amine, 0.41 g (0.35 mmol) of tetrakis(triphenylphosphine)palladium, 23 ml of 2M $Na_2CO_3$, 100 ml of EtOH and 200 ml toluene was degassed and placed under nitrogen, and then heated at 100° C. for 8 hours. After finishing the reaction, the mixture was allowed to cool to room temperature. The organic layer was extracted with dichloromethane and water, dried with anhydrous magnesium sulfate, the solvent was removed and the residue was purified by column chromatography on silica (hexane-dichloromethane) to give product 17.5 g (yield 55%) as a yellow solid. MS (m/z, FAB$^+$): 902.3; $^1$H NMR (CDCl$_3$, 500 MHz): chemical shift (ppm) 8.97 (s, 1H), 8.80 (d, J=8.0 Hz, 1H), 8.75 (d, J=8.0 Hz, 1H), 8.68 (s, 1H), 8.67 (d, J=8.0 Hz, 2H), 7.98 (d, J=8.0 Hz, 1H), 7.77~7.63 (m, 9H), 7.59 (d, J=8 Hz, 1H), 7.52 (d, J=7.5 Hz, 2H), 7.47~7.41 (d, 2H), 7.41~7.28 (m, 8H), 7.16~7.05 (m, 8H), 6.84 (d, J=7.5 Hz, 2H), 6.68 (d, J=7.5 Hz, 2H), 1.59 (s, 6H)

EXAMPLE 2

Synthesis of Derivative A8

Synthesis of N-(9,9'-spirobifluorene-2-yl)-N-(biphenyl-4-yl)-10,10-dimethyl-10H-indeno[1,2-b]triphenylen-12-amine

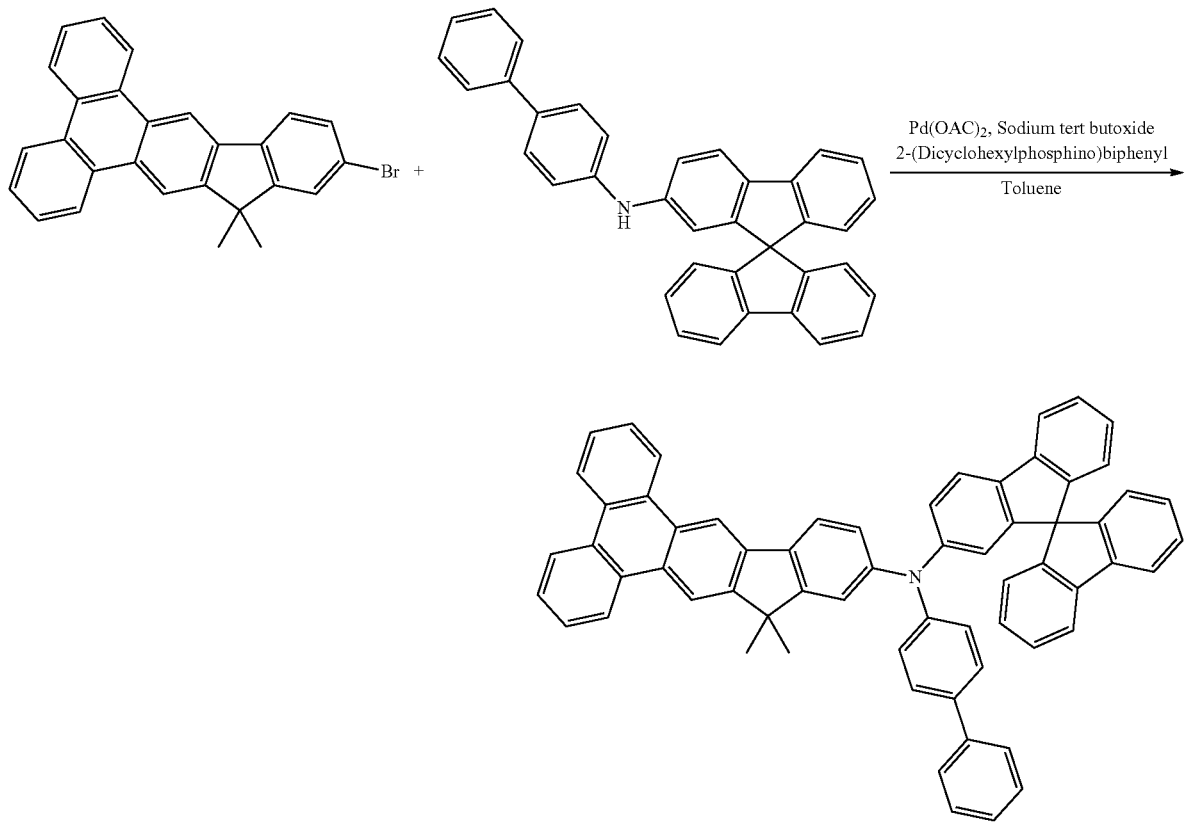

A mixture of 5 g (11.8 mmol) 12-bromo-10,10-dimethyl-10H-indeno[1,2-b]triphenylene, 6.8 g (14.1 mmol) of N-(biphenyl-4-yl)-9,9'-spirobi fluorene-2-amine, 0.03 g (0.11 mmol) of palladium(II)acetate, 0.04 g (0.11 mmol) of 2-(dicyclohexylphosphino)biphenyl, 1.7 g (17.7 mmol) of sodium tert-butoxide and 100 ml of toluene was refluxed under nitrogen overnight. After finishing the reaction, than cooled to room temperature. The organic layer was extracted with dichloromethane and water, dried with anhydrous magnesium sulfate, the solvent was removed and the residue was purified by column chromatography on silica (hexane-dichloromethane) to give product 5.8 g (yield 60%) as a yellow solid. MS (m/z, FAB$^+$): 826.3; $^1$H NMR (CDCl$_3$, 500 MHz): chemical shift (ppm) 8.78 (s, 1H), 8.73 (d, J=8.0 Hz, 2H), 8.70 (d, J=8.0 Hz, 2H), 8.78 (s, 1H), 7.77~7.61 (m, 9H), 7.56 (d, J=7.5 Hz, 2H), 7.44~7.39 (m, 4H), 7.34~7.26 (m, 4H), 7.15~6.97 (m, 8H), 6.85 (d, J=7.5 Hz, 2H), 6.67~6.64 (m, 2H), 1.35 (s, 6H)

EXAMPLE 3

Synthesis of Derivative A14

Synthesis of N-(biphenyl-4-yl)-9,9'-spirobifluorene-4-amine

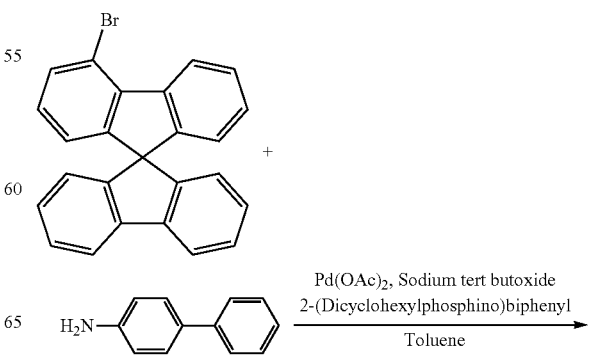

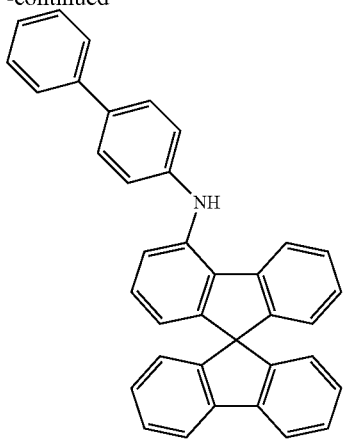

A mixture of 30 g (75.8 mmol) 4-bromo-9,9'-spirobi[fluorene], 15.3 g (90.9 mmol) of biphenyl-4-amine, 0.17 g (0.76 mmol) of palladium(II) acetate, 0.26 g (0.76 mmol) of 2-(dicyclohexylphosphino)biphenyl, 9.5 g (98.5 mmol) of sodium tert-butoxide and 300 ml of toluene was refluxed under nitrogen overnight. After finishing the reaction, than cooled to room temperature. The organic layer was extracted with dichloromethane and water, dried with anhydrous magnesium sulfate, the solvent was removed and the residue was purified by column chromatography on silica (hexane-dichloromethane) to give product 19.0 g (yield 52%) as a white solid.

Synthesis of N-(9,9'-spirobifluorene-4-yl)-N-(biphenyl-4-yl)-10,10-dimethyl-10H-indeno[1,2-b]triphenylen-13-amine

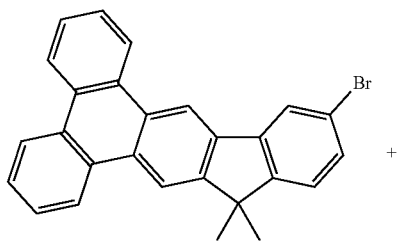

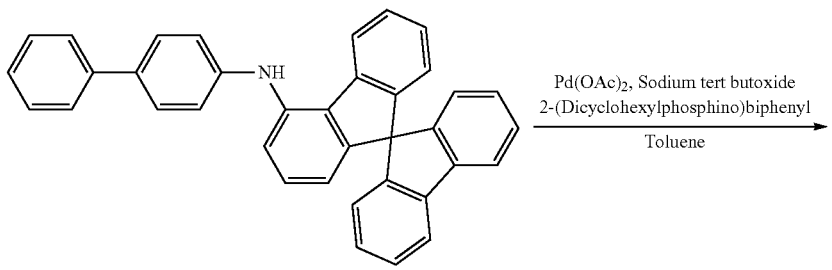

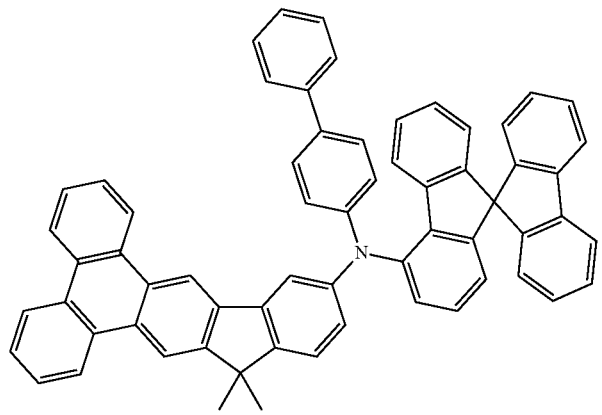

A mixture of 4.5 g (10.6 mmol) 13-bromo-10,10-dimethyl-10H-indeno[1,2-b]triphenylene, 6.1 g (12.7 mmol) of N-(biphenyl-4-yl)-9,9'-spirobifluorene-4-amine, 0.03 g (0.11 mmol) of palladium(II)acetate, 0.04 g (0.11 mmol) of 2-(dicyclohexylphosphino)biphenyl, 1.3 g (13.8 mmol) of sodium tert-butoxide and 100 ml of toluene was refluxed under nitrogen overnight. After finishing the reaction, than cooled to room temperature. The organic layer was extracted with dichloromethane and water, dried with anhydrous magnesium sulfate, the solvent was removed and the residue was purified by column chromatography on silica (hexane-dichloromethane) to give product 4.8 g (yield 55%) as a yellow solid. MS (m/z, FAB⁺): 826.5; ¹H NMR (CDCl₃, 500 MHz): chemical shift (ppm) 8.81 (s, 1H), 8.75 (d, J=8.0 Hz, 1H), 8.67~8.65 (m, 3H), 7.89~7.83 (m, 4H), 7.67~7.54 (m, 8H), 7.44~7.25 (m, 8H), 7.21~7.10 (m, 6H), 7.01 (t, 1H), 6.83 (b, 2H), 6.69 (d, J=7.0 Hz, 1H), 1.65 (s, 6H)

EXAMPLE 4

Synthesis of Derivative A18

Synthesis of N,N-di(biphenyl-4-yl)-10,10-dimethyl-10H-indeno[2,1-b]triphenylen-12-amine

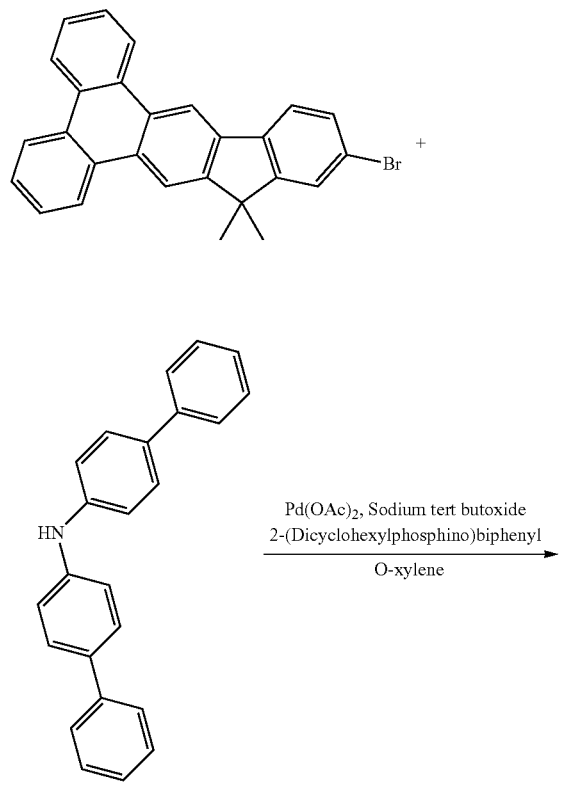

-continued

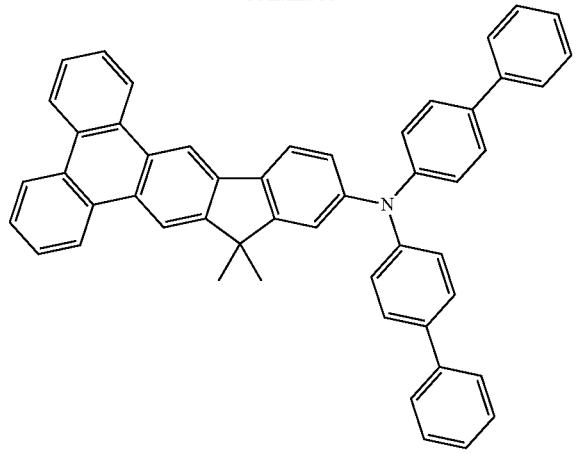

A mixture of 4.3 g (10.1 mmol) 12-bromo-10,10-dimethyl-10H-indeno[2,1-b]triphenylene, 3.9 g (12.1 mmol) of dibiphenyl-4-ylamine, 0.05 g (0.2 mmol) of palladium(II) acetate, 0.15 g (0.4 mmol) of 2-(dicyclohexyl phosphine) biphenyl, 2 g (20 mmol) of sodium tert-butoxide and 50 ml of o-xylene was refluxed under nitrogen overnight. After finishing the reaction, the solution was filtered at 100° C., to receive the filtrate, and the filtrate was added to 500 ml MeOH, while stirring and the precipitated product was filtered off with suction. The product was purified by sublimation to get 2.9 g of product (yield 37%). MS (m/z, FAB⁺): 663.1; ¹H NMR (CDCl₃, 500 MHz): chemical shift (ppm) 8.88 (s, 1H), 8.79 (d, J=8.0 Hz, 1H), 8.72 (d, J=8.0 Hz, 1H), 8.66 (d, J=5.0 Hz, 2H), 8.63 (s, 1H), 7.85 (d, J=8.0 Hz, 1H), 7.69~7.63 (m, 4H), 7.61 (d, J=7.5 Hz, 4H), 7.54 (d, J=8.5 Hz, 4H), 7.44~7.41 (t, 4H), 7.33~7.26 (m, 7H), 7.20 (d, J=8.0 Hz, 1H), 1.59 (s, 6H)

EXAMPLE 5

Synthesis of Derivative A19

Synthesis of 3-bromo-N-(4-bromophenyl)aniline

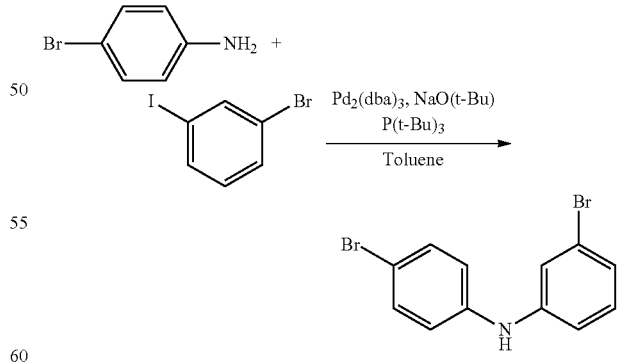

A mixture of 32.5 g (114.9 mmol) of 1-bronco-3-iodobenzene, 14.1 g (81.9 mmol) of 4-bromoaniline, 23.6 g (245.8 mmol) of sodium t-butoxide and 2 ml (8.2 mmol) of tri-t-butylphosphine were dissolved in 400 ml of toluene, 1.5 g (1.64 mmol) of Pd₂ (dba)₃ was added thereto, and then the mixture was stirred while refluxing overnight. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl acetate as eluent to get 12.6 g (yield 47%) of product.

Synthesis of 3-(dibenzo[b,d]furan-4-yl)-N-(4-(dibenzo[b,d]furan-4-yl)phenyl) aniline

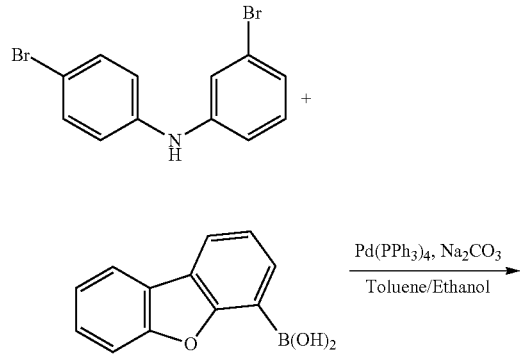

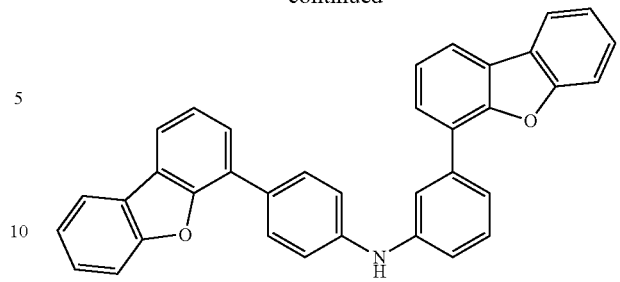

A mixture of 9.8 g (30 mmol) of 3-bromo-N-(4-bromophenyl) aniline, 14 g (66 mmol) of dibenzo[b,d]furan-4-ylboronic acid, 0.69 g (0.6 mmol) of tetrakis(triphenylphosphine)palladium, 60 ml of 2M $Na_2CO_3$, 60 ml of EtOH and 150 ml toluene was degassed and placed under nitrogen, and then heated at 110° C. overnight. After finishing the reaction, the mixture was allowed to cool to room temperature. Than 100 ml of MeOH was added, while stirring and the precipitated product was filtered off with suction. To give 9.8 g (yield 65%) of yellow product which was recrystallized from ethyl acetate.

Synthesis of N-(3-(dibenzo[b,d]furan-4-yl)phenyl)-N-(4-(dibenzo[b,d]furan-4-yl)phenyl)-10,10-dimethyl-10H-indeno[2,1-b]triphenylen-12-amine

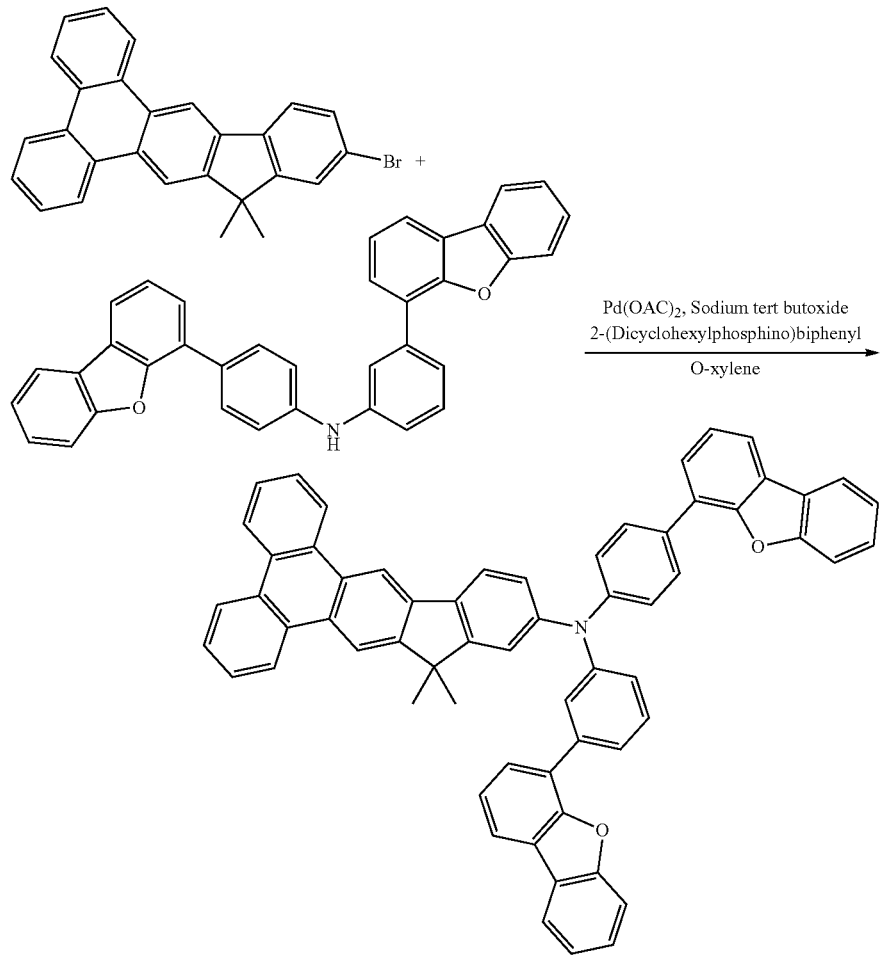

A mixture of 4.3 g (10.1 mmol) 12-bromo-10,10-dimethyl-10H-indeno[2,1-b]triphenylene, 6.1 g (12.1 mmol) of 3-(dibenzo[b,d]furan-4-yl)-N-(4-(dibenzo[b,d]furan-4-yl)phenyl)aniline, 0.05 g (0.2 mmol) of palladium(II) acetate, 0.15 g (0.4 mmol) of 2-(dicyclohexylphosphino)biphenyl, 2 g (20 mmol) of sodium tert-butoxide and 50 ml of o-xylene was refluxed under nitrogen overnight. After finishing the reaction, the solution was filtered at 100° C., to receive the filtrate, and the filtrate was added to 500 ml MeOH, while stirring and the precipitated product was filtered off with suction. The product was purified by sublimation to get 4.0 g of product (yield 47%). MS (m/z, FAB$^+$): 843.3; $^1$H NMR (CDCl$_3$, 500 MHz): chemical shift (ppm) 8.90 (s, 1H), 8.81 (d, J=8.0 Hz, 1H), 8.74 (d, J=8.0 Hz, 1H), 8.68 (d, J=5.0 Hz, 2H), 8.61 (s, 1H), 8.1~7.94 (m, 3H), 7.69~7.54 (m, 12H), 7.44~7.38 (m, 6H), 7.33~7.26 (m, 7H), 7.20 (d, J=8.0 Hz, 1H), 1.61 (s, 6H)

EXAMPLE 6

Synthesis of Derivative A21

Synthesis of N-(4-bromophenyl)biphenyl-4-amine

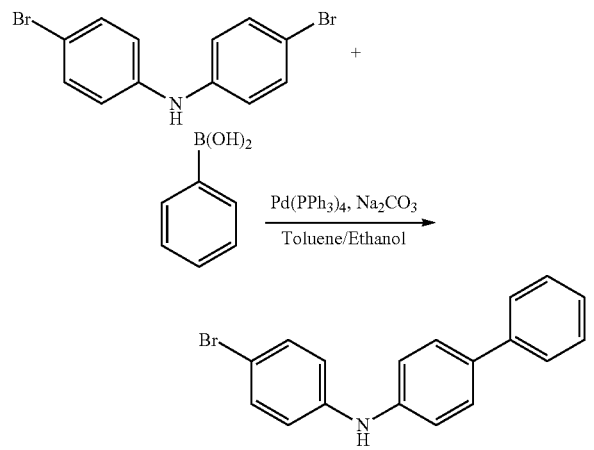

A mixture of 14.7 g (45 mmol) of bis(4-bromophenyl)amine, 5.5 g (45 mmol) of phenylboronic acid, 0.51 g (0.45 mmol) of tetrakis(triphenyl-phosphine)palladium, 45 ml of 2M Na$_2$CO$_3$, 45 ml of EtOH and 90 ml toluene was degassed and placed under nitrogen, and then heated at 90° C. overnight. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl acetate as eluent to get 5.2 g (yield 36%) of product.

Synthesis of N-(4-(9-phenyl-9H-carbazol-3-yl)phenyl)biphenyl-4-amine

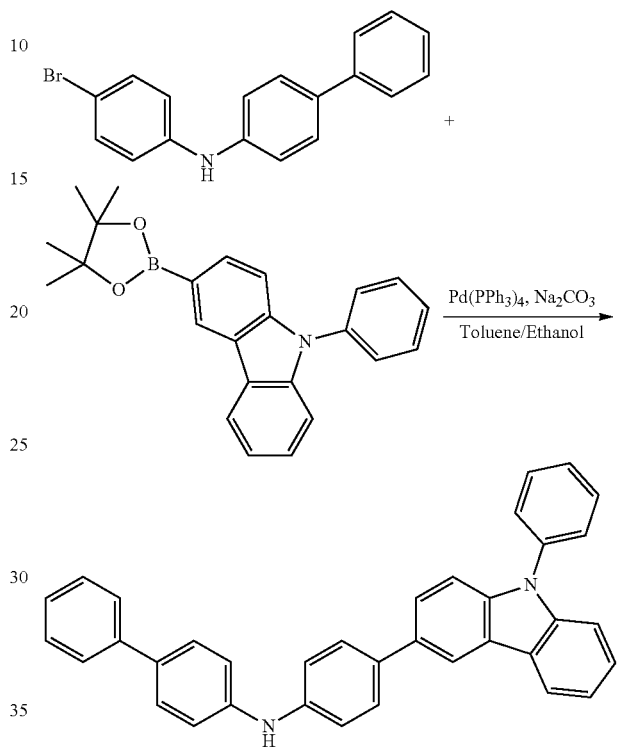

A mixture of 5.2 g (16 mmol) of N-(4-bromophenyl)biphenyl-4-amine, 6.6 g (18 mmol) of 9-phenyl-3-(4,4,5,5-tetramethyl-1,3,2-dioxaborolan-2-yl)-9H-carbazole, 0.37 g (0.32 mmol) of tetrakis(triphenyl-phosphine) palladium, 16 ml of 2M Na$_2$CO$_3$, 20 ml of EtOH and 50 ml toluene was degassed and placed under nitrogen, and then heated at 90° C. overnight. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl acetate as eluent to get 5.0 g (yield 64%) of product.

Synthesis of N-(biphenyl-4-yl)-10,10-dimethyl-N-(4-(9-phenyl-9H-carbazol-3-yl)phenyl)-10H-indeno[2,1-b]triphenylen-12-amine

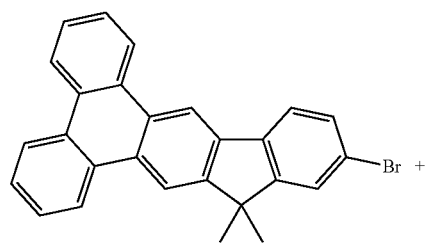

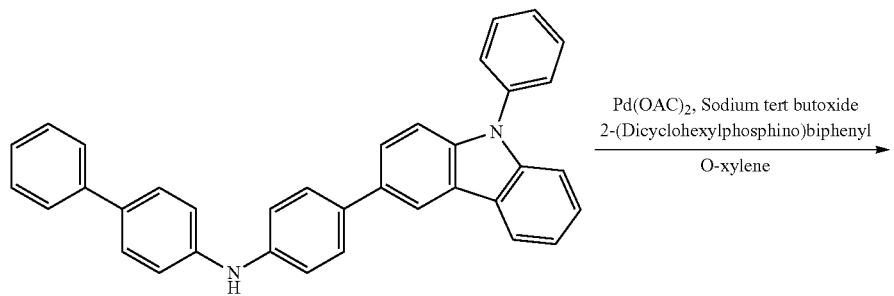

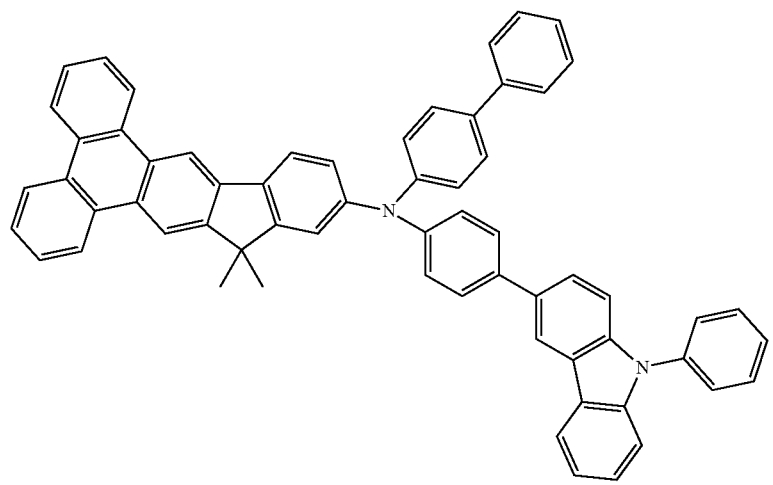

A mixture of 4.3 g (10.1 mmol) 12-bromo-10,10-dimethyl-10H-indeno[2,1-b]triphenylene, 5.0 g (10.2 mmol) of 3-(dibenzo[b,d]furan-4-yl)-N-(4-(dibenzo[b,d]furan-4-yl) phenyl)aniline, 0.05 g (0.2 mmol) of palladium(II) acetate, 0.15 g (0.4 mmol) of 2-(dicyclohexylphosphino)biphenyl, 2 g (20 mmol) of sodium tert-butoxide and 50 ml of o-xylene was refluxed under nitrogen overnight. After finishing the reaction, 500 ml MeOH was added, while stirring and the precipitated product was filtered off with suction. The product was purified by sublimation to get 5.1 g of product (yield 61%). MS (m/z, FAB$^+$): 828.6; $^1$H NMR (CDCl$_3$, 500 MHz): chemical shift (ppm) 8.86 (s, 1H), 8.81 (d, J=8.0 Hz, 1H), 8.72 (d, J=8.0 Hz, 1H), 8.66 (d, J=5.0 Hz, 2H), 8.59 (s, 1H), 8.37 (s, 1H), 8.11~7.94 (m, 4H), 7.74~7.47 (m, 12H), 7.44~7.38 (m, 6H), 7.31~7.23 (m, 8H), 7.20 (d, J=8.0 Hz, 1H), 1.61 (s, 6H)

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis (phenyl)-benzidine (NPB) is most widely used as the hole transporting layer. 10,10-Dimethyl-12-(4-(pyren-1-yl)phenyl)-10H-indeno[1,2-b]triphenylene (PT-312, US20140175384) is used as blue emitting host in organic EL device, and N1,N1,N6,N6-tetram-tolylpyrene-1,6-diamine (D1) is used as blue guest. 2-(10,10-dimethyl-10H-indeno[2,1-b]triphenylen-13-yl)-4,6-bis-5-phenylbiphenyl-3-yl)-1,3,5-triazine (ET3) is used as electron transporting material to co-deposit with 8-hydroxyquinolato-lithium (LiQ) in organic EL device. Tris(2-phenylpyridinato)iridium(III) (D2) is used as phosphorescent dopant. H2 (US 20140166988A1, see the below chemical structure) is used as phosphorescent host for organic EL device. The prior art of OLED materials for producing standard organic EL device control and comparable material in this invention shown its chemical structure as following:

-continued
HAT-CN
NPB
D1
PT-312
LiQ
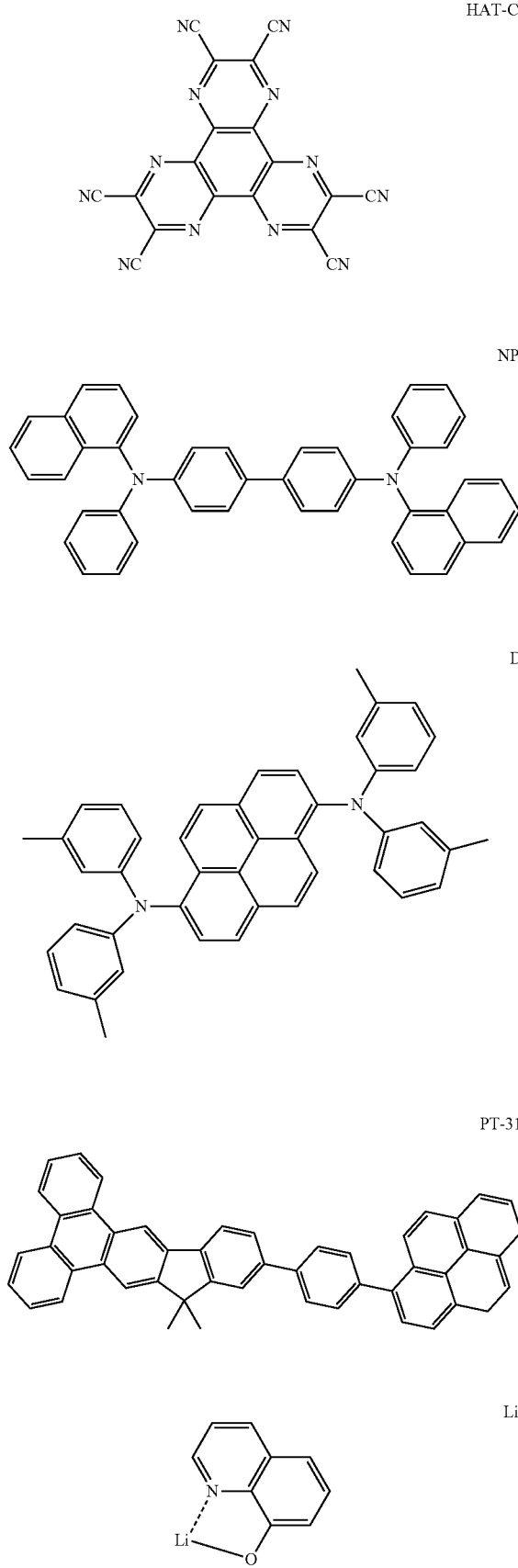
ET3
H2
D2
A1
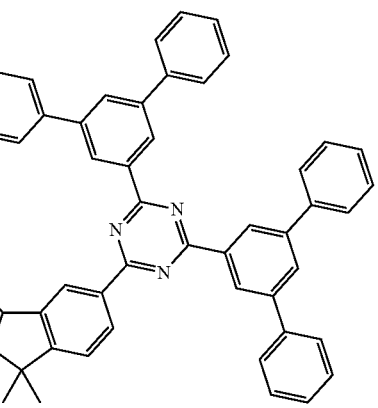
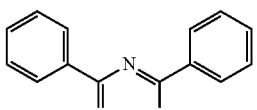
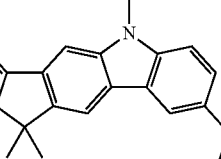
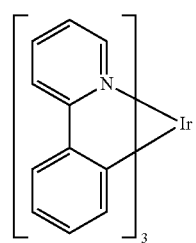
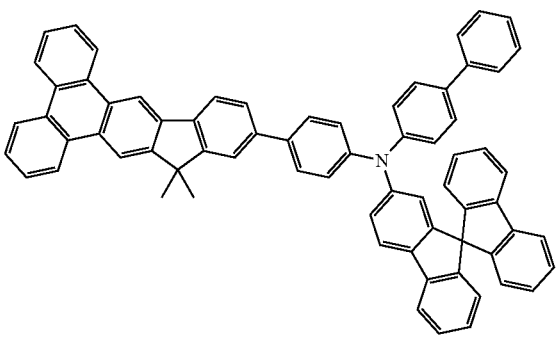

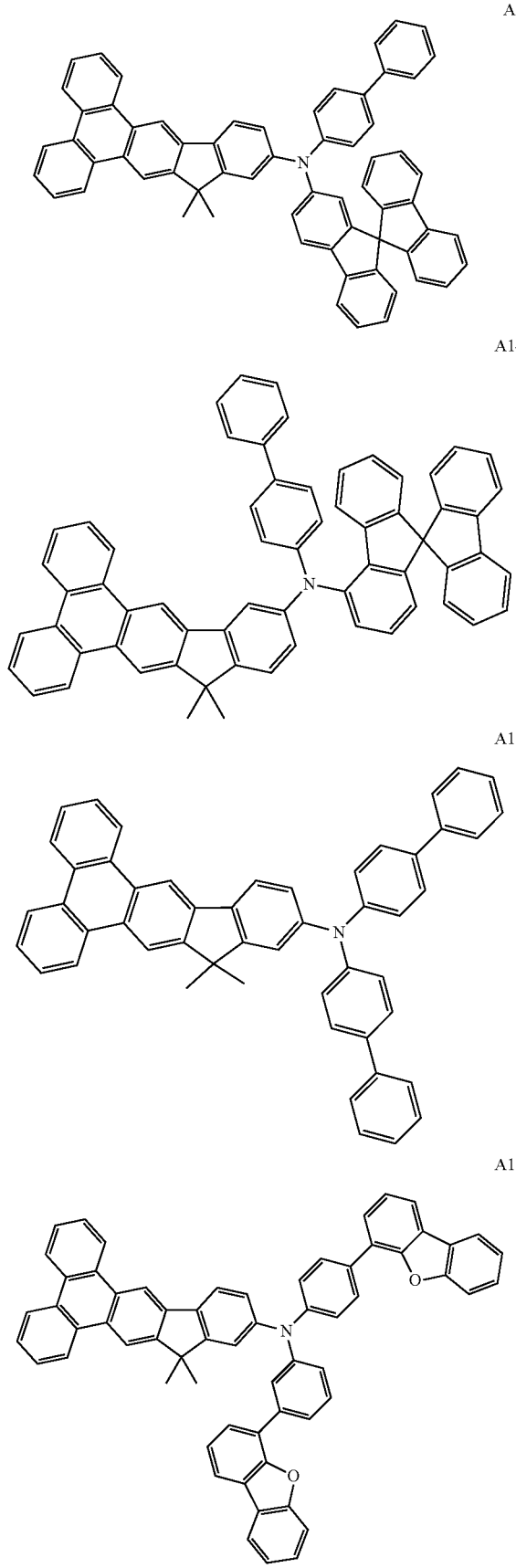

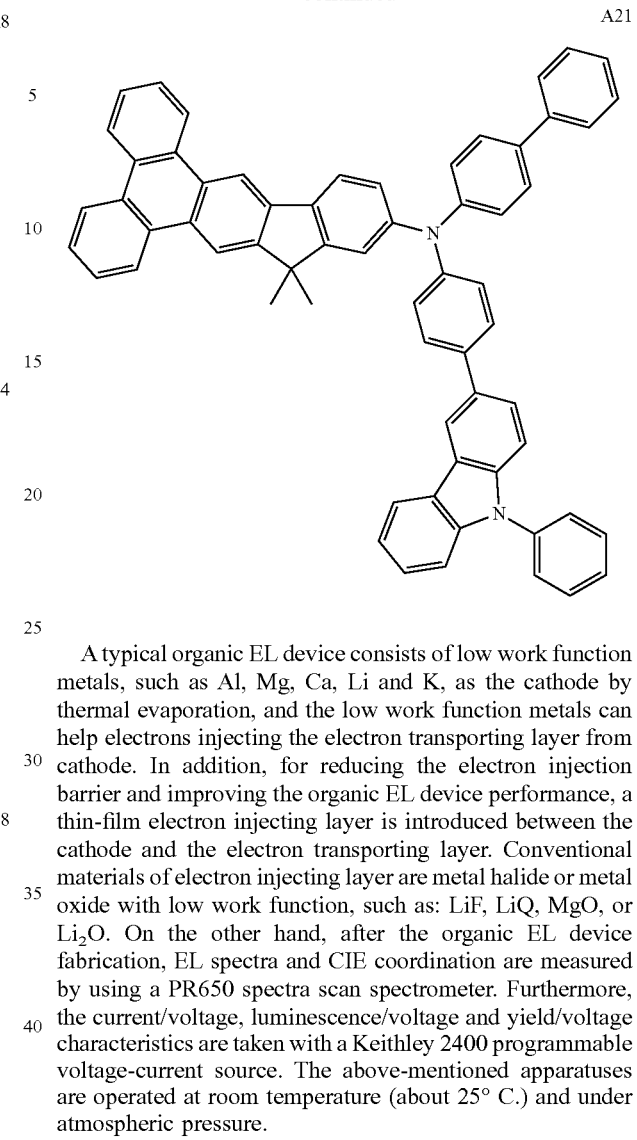

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 7

Using a procedure analogous to the above mentioned general method, fluorescent blue-emitting organic EL device having the following device structure I was produced (See FIG. 1). Device I: ITO/HAT-CN (20 nm)/hole transport material (HTM) (110 nm)/electron blocking material (EBM) (5 nm)/PT-312 doped 5% D1 (30 nm)/ET3 co-deposit 50% LiQ (40 nm)/LiF (0.5 nm)/Al (160 nm). The I-V-B (at 1000 nits) and half-life time of fluorescent blue-emitting organic EL device testing report as Table 1. The half-life time is defined that the initial luminance of 1000 cd/m² has dropped to half.

TABLE 1

| HTM | EBM | Voltage (V) | Efficiency (cd/A) | CIE (y) | Half-life time (hour) |
|---|---|---|---|---|---|
| NPB | — | 5.0 | 4.3 | 0.172 | 180 |
| A21 | — | 5.0 | 4.8 | 0.175 | 260 |
| NPB | A1 | 5.2 | 4.9 | 0.175 | 350 |
| NPB | A8 | 5.2 | 5.3 | 0.175 | 380 |

TABLE 1-continued

| HTM | EBM | Voltage (V) | Efficiency (cd/A) | CIE (y) | Half-life time (hour) |
|---|---|---|---|---|---|
| NPB | A14 | 5.0 | 5.0 | 0.174 | 350 |
| A21 | A18 | 4.8 | 5.4 | 0.175 | 280 |
| NPB | A19 | 4.8 | 5.1 | 0.174 | 450 |

EXAMPLE 8

Using a procedure analogous to the above mentioned general method, phosphorescent emitting organic EL device having the following device structures are produced (See FIG. 1.): Device I: ITO/HAT-CN (20 nm)/hole transport material (HTM) (110 nm)/electron blocking material (EBM) (5 nm)/H2 doped 12% D2 (35 nm)/ET3 co-deposit 50% LiQ (40 nm)/LiF (0.5 nm)/Al (160 nm). The I-V-B (at 1000 nits) and half-life time of phosphorescent emitting organic EL device testing report as Table 2. The half-life time is defined that the initial luminance of 3000 cd/m² has dropped to half.

TABLE 2

| HTM | EBM | Voltage (V) | Efficiency (cd/A) | CIE (x, y) | Half-life time (hour) |
|---|---|---|---|---|---|
| NPB | — | 3.8 | 42 | 0.352, 0.612 | 620 |
| A21 | — | 3.2 | 48 | 0.353, 0.613 | 810 |
| NPB | A1 | 3.2 | 49 | 0.352, 0.613 | 850 |
| NPB | A8 | 3.2 | 53 | 0.352, 0.613 | 880 |
| NPB | A14 | 3.5 | 50 | 0.353, 0.612 | 860 |
| NPB | A18 | 3.0 | 48 | 0.353, 0.612 | 700 |
| NPB | A19 | 3.2 | 51 | 0.353, 0.612 | 715 |
| NPB | A21 | 3.3 | 46 | 0.352, 0.613 | 960 |

In the above preferred embodiments for organic EL device test report (see Table 1 and Table 2), we show that with a general formula (A) in the present invention display good performance and shown lower power consumption, higher efficiency and longer half-life time.

To sum up, the present invention discloses an indenotriphenylene-based amine derivative which can be used for organic EL device. More specifically, an organic EL device employing the derivative as a hole transport material or an electron blocking material is disclosed. The mentioned derivative is represented by the following formula (A):

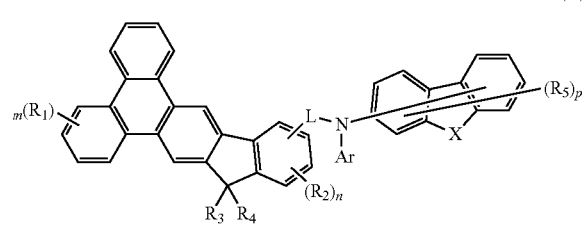

formula (A)

wherein L represent a single bond, a substituted or unsubstituted divalent arylene group having 6 to 30 carbon atoms; m represents an integer of 0 to 10; n represents an integer of 0 to 3; p represents an integer of 0 to 7; X is absent or represents a divalent bridge selected from the atom or group consisting from O, S, C(R$_6$)(R$_7$), and NR$_8$; R$_1$ to R$_8$ are independently selected from the group consisting of a hydrogen atom, a substituted or unsubstituted alkyl group having 1 to 20 carbon atoms, a substituted or unsubstituted aryl group having 6 to 30 carbon atoms, and a substituted or unsubstituted heteroaryl group having 3 to 30 carbon atoms; Ar is selected from the group consisting of a substituted or unsubstituted aryl group having 6 to 50 carbon atoms, and a substituted or unsubstituted heteroaryl group having 3 to 50 carbon atoms.

The invention claimed is:

1. An indenotriphenylene-based amine derivative with a general formula (A) as following:

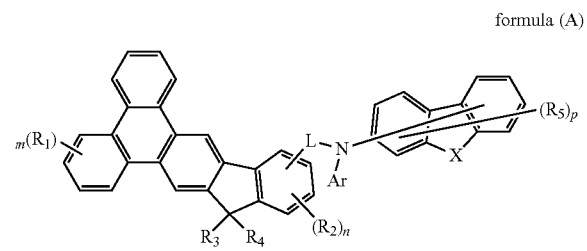

formula (A)

wherein L represents a single bond, a substituted or unsubstituted divalent arylene group having 6 to 30 carbon atoms; m represents an integer of 0 to 10; n represents an integer of 0 to 3; p represents an integer of 0 to 7; X is absent or represents a divalent bridge selected from the atom or group consisting from O, S, C(R$_6$)(R$_7$), and NR$_8$; R$_1$ to R$_8$ are independently selected from the group consisting of a hydrogen atom, a substituted or unsubstituted alkyl group having 1 to 20 carbon atoms, a substituted or unsubstituted aryl group having 6 to 30 carbon atoms, and a substituted or unsubstituted heteroaryl group having 3 to 30 carbon atoms; Ar is selected from the group consisting of a substituted or unsubstituted aryl group having 6 to 50 carbon atoms, and a substituted or unsubstituted heteroaryl group having 3 to 50 carbon atoms.

2. The indenotriphenylene-based amine derivative according to claim 1, wherein L represents one of the following:

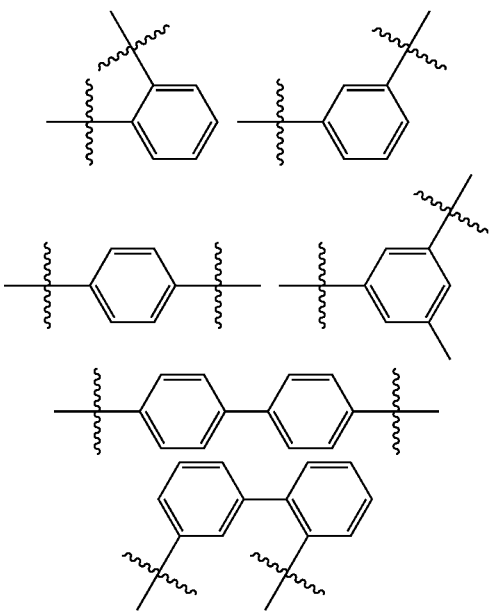

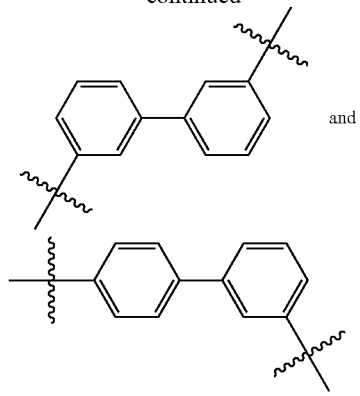
3. The indenotriphenylene-based amine derivative according to claim 1, wherein Ar represents one of the following:
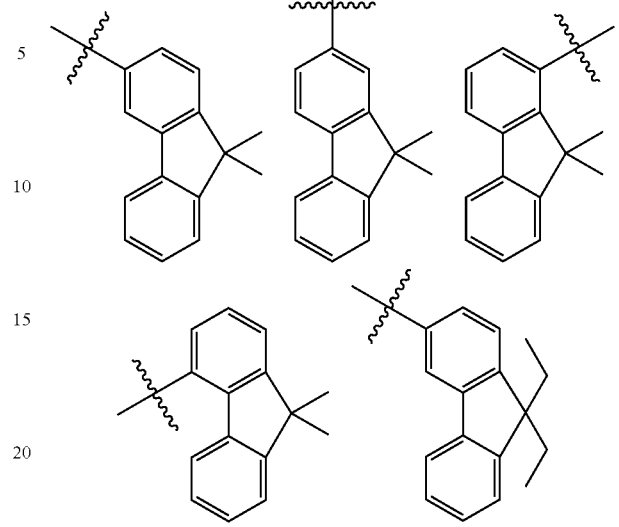
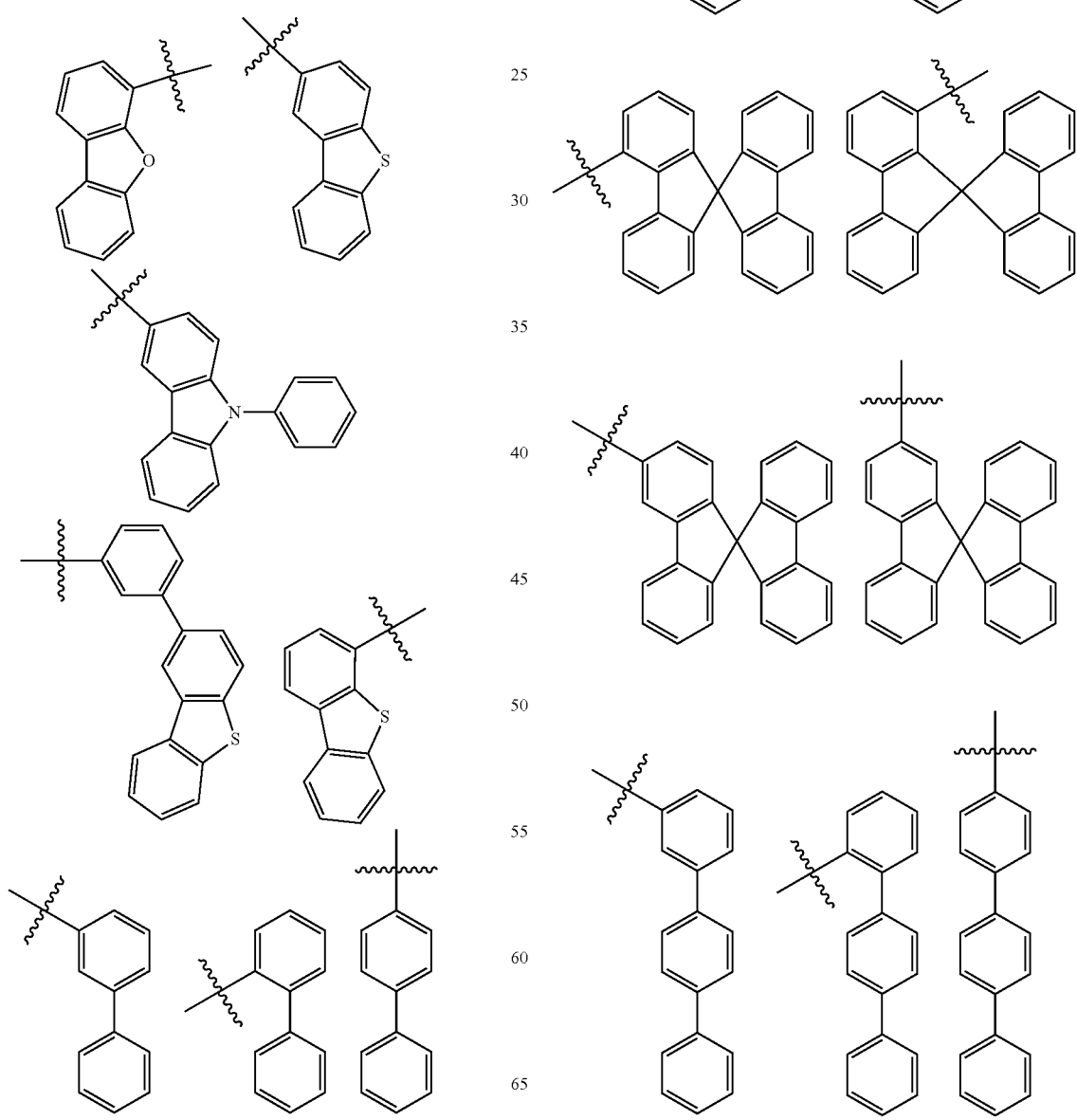

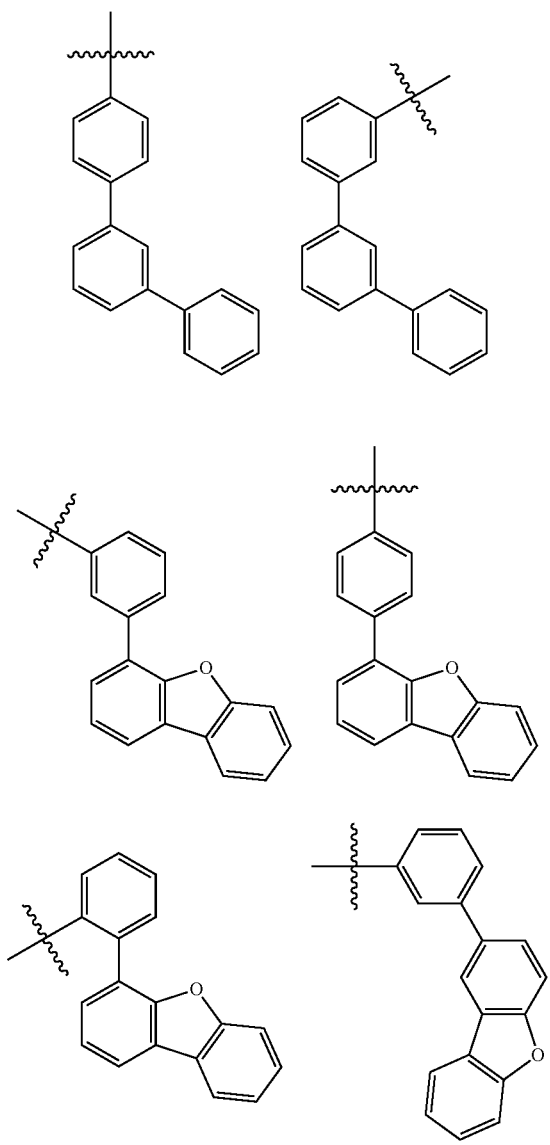
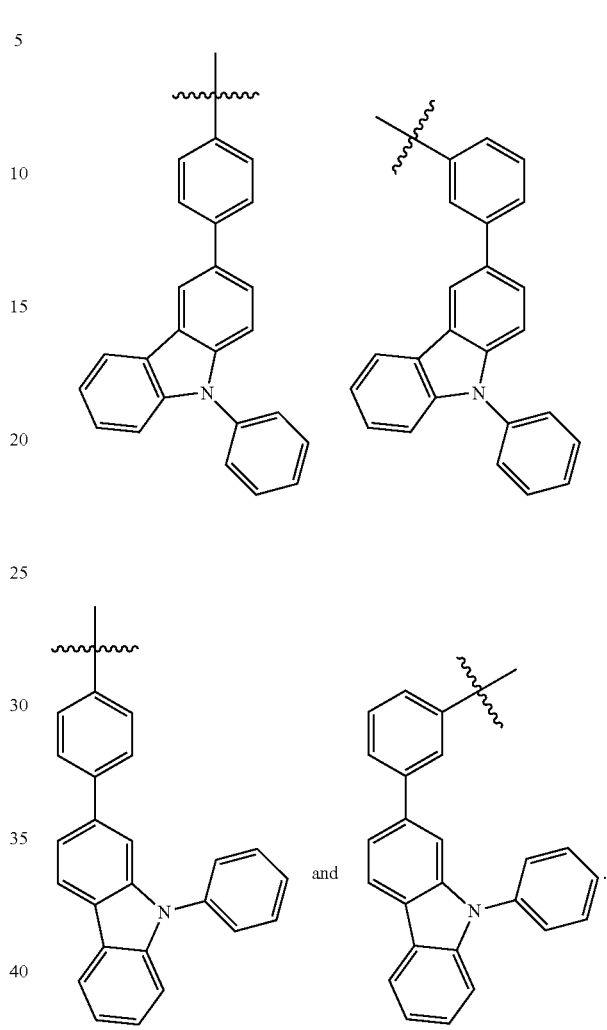
4. The indenotriphenylene-based amine derivative according to claim 1, wherein the indenotriphenylene-based amine derivative is selected from the group consisting of
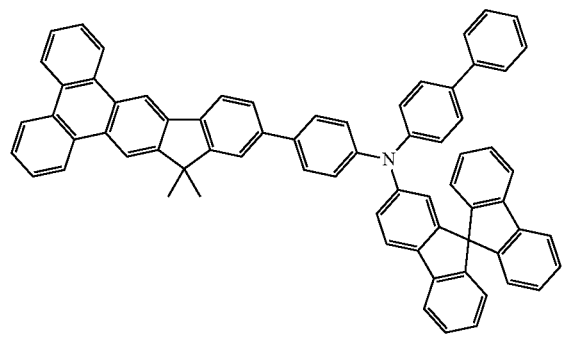

A3
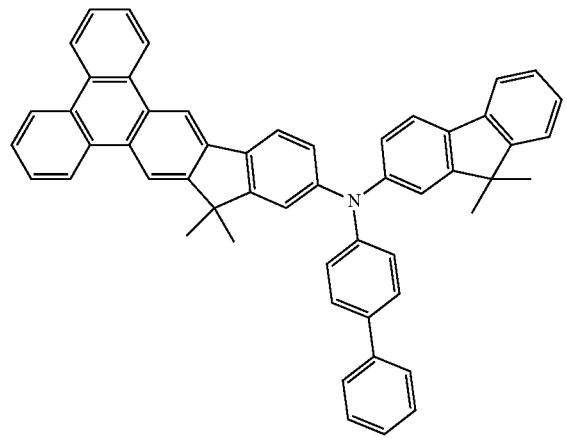
A4
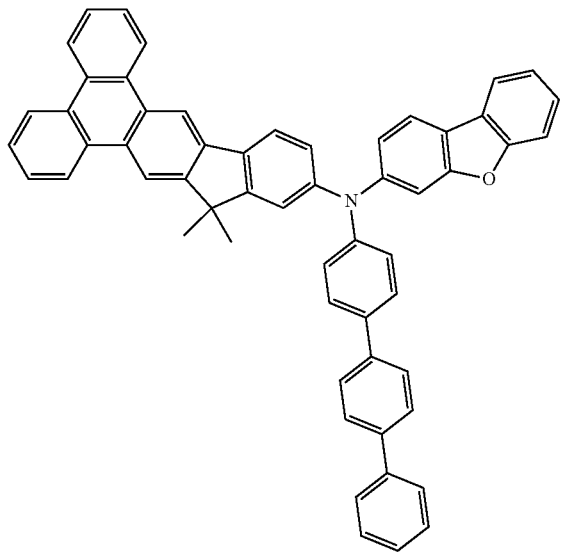
A5
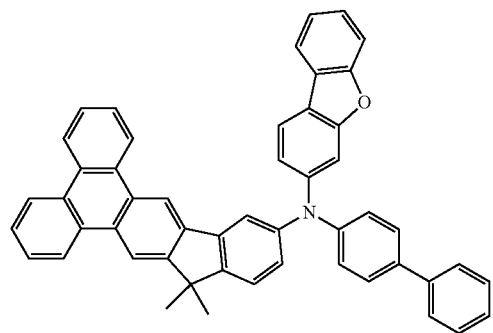
A6
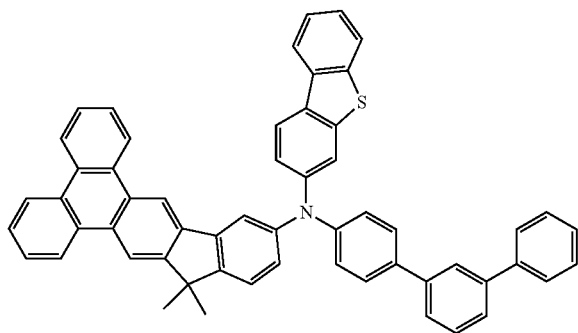
A7
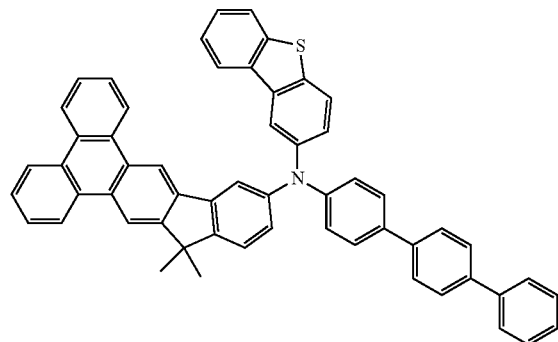
A8
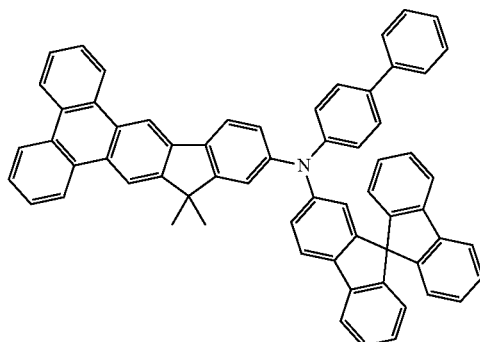

-continued
A9
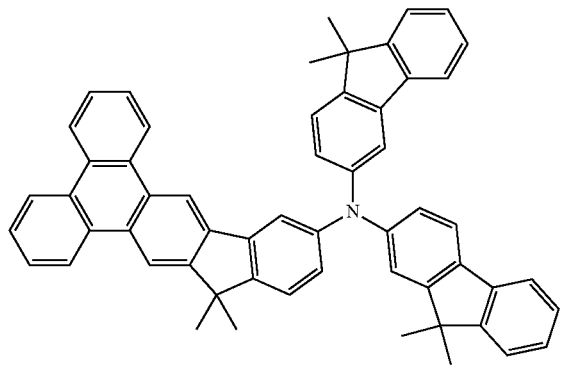
A10
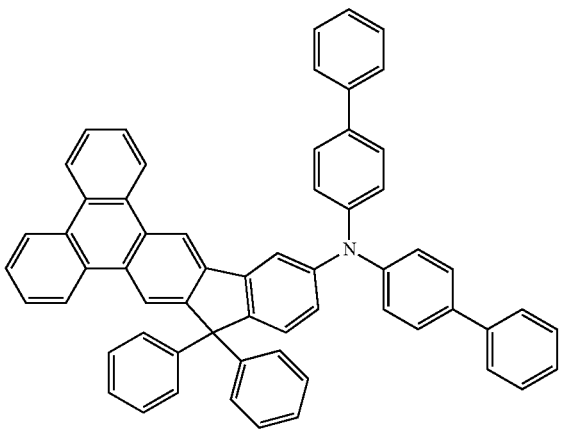
A11
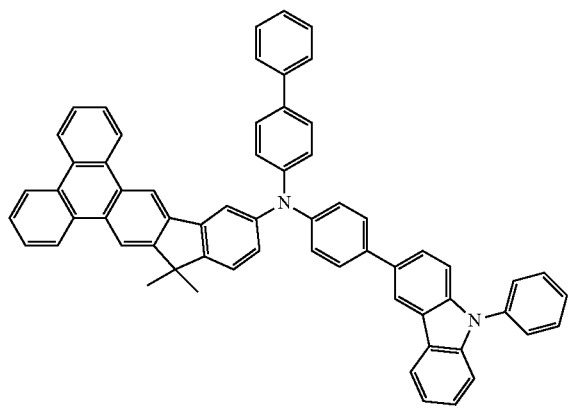
A12
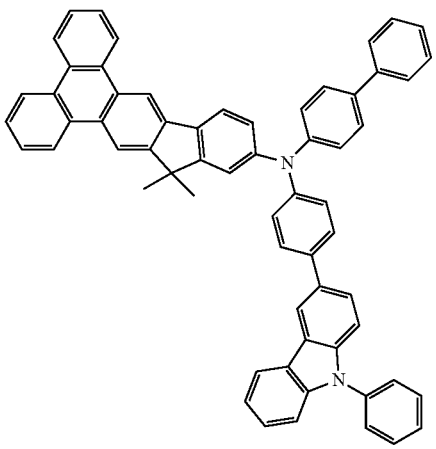
A13
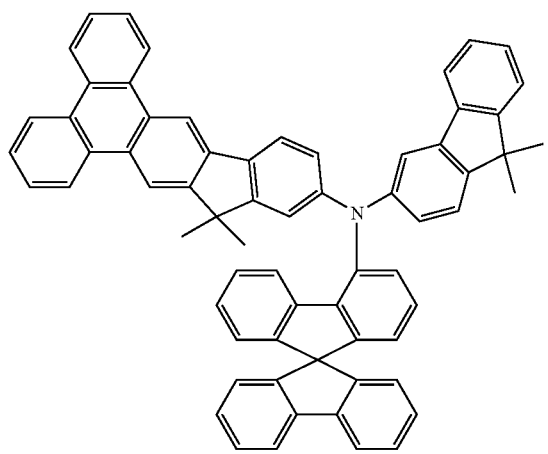
A14
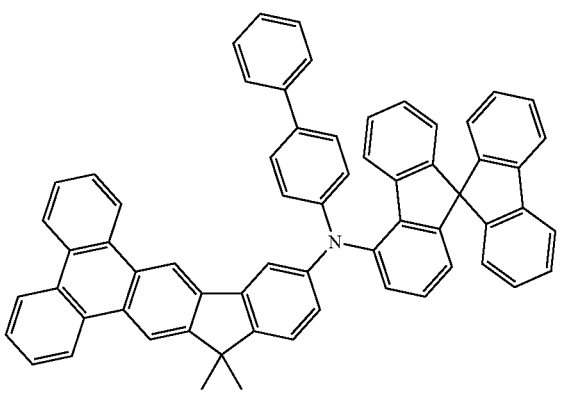

-continued
A15
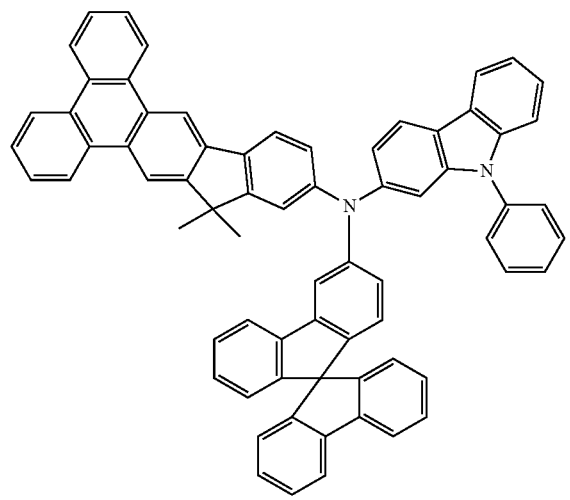
A16
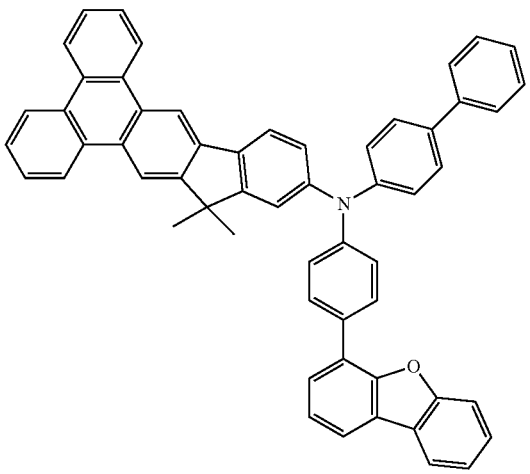
A17
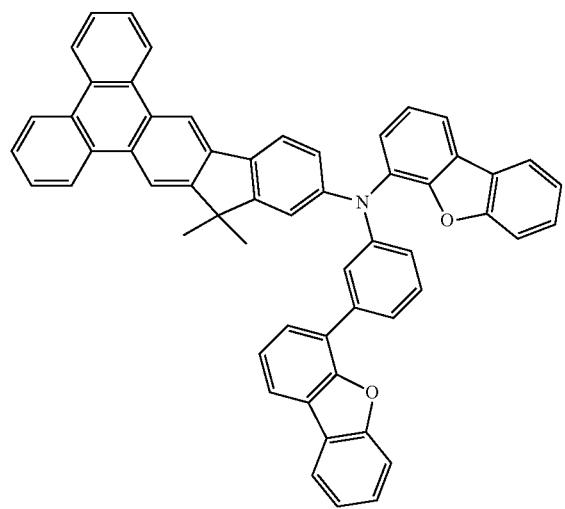
A18
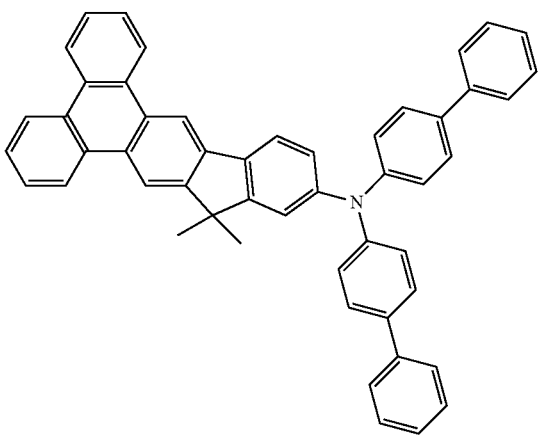
A19
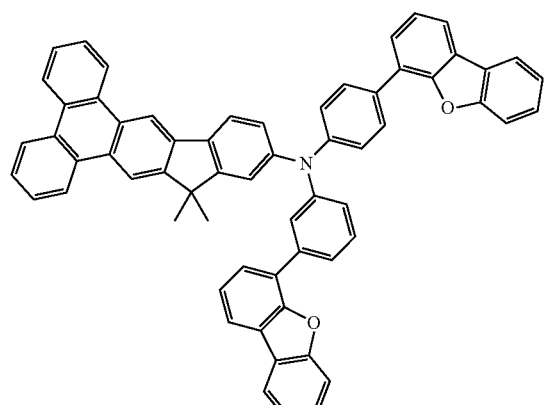
A20
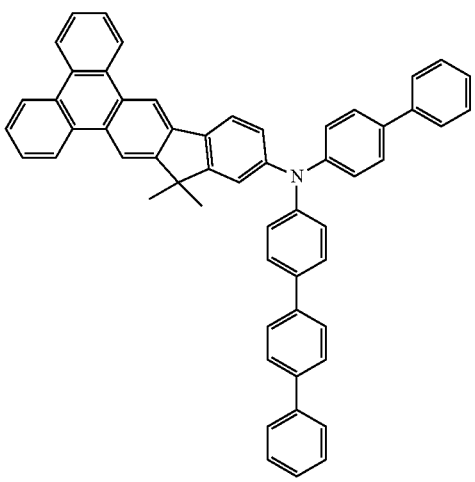

-continued
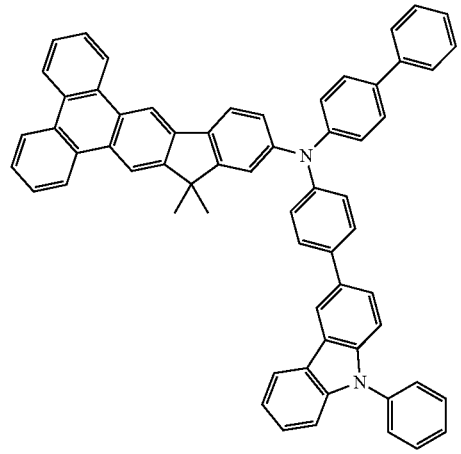
A21
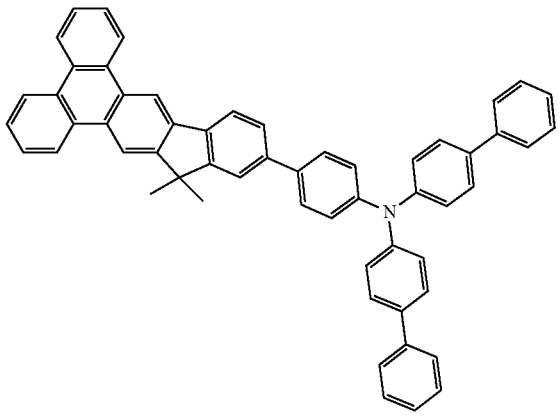
A22
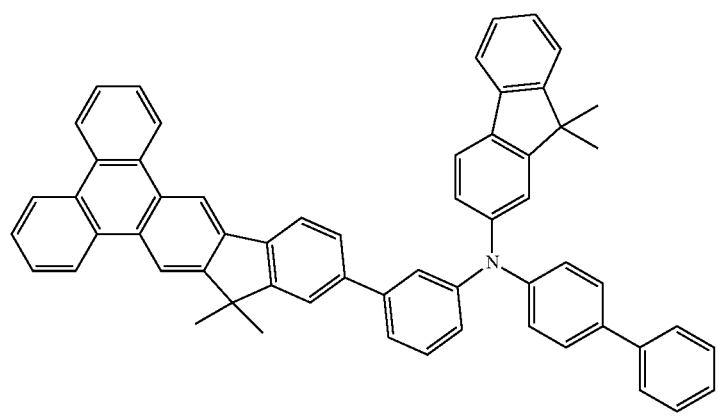
A23
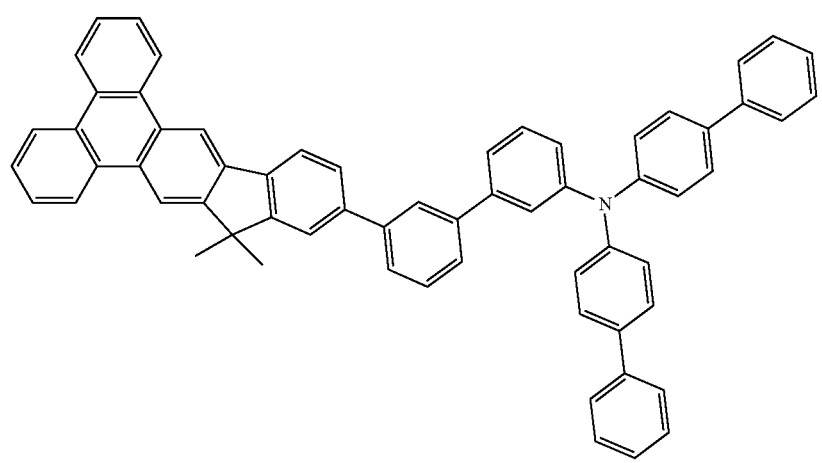
A24

-continued
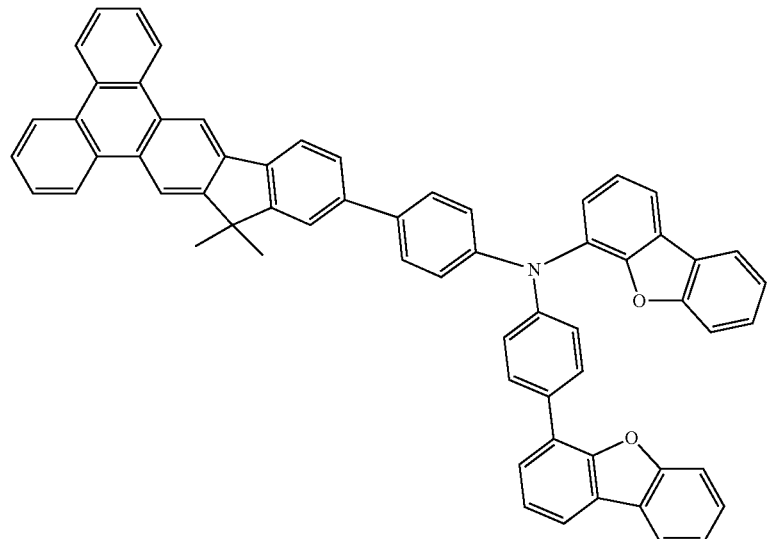
A25
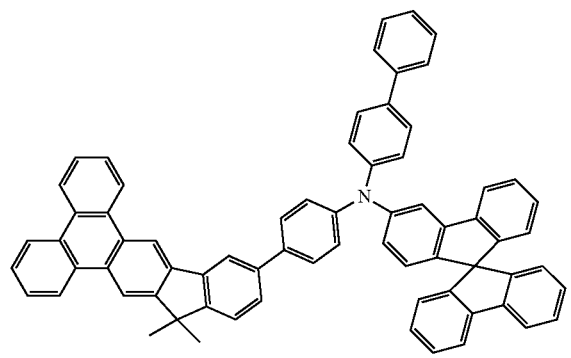
A26
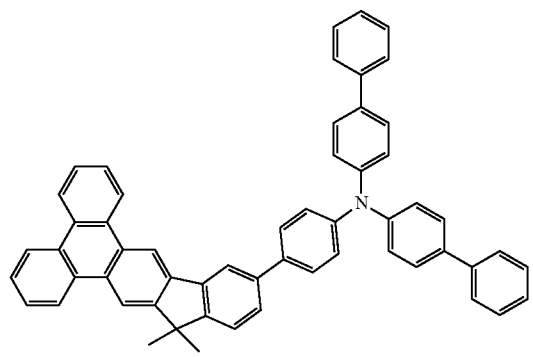
A27
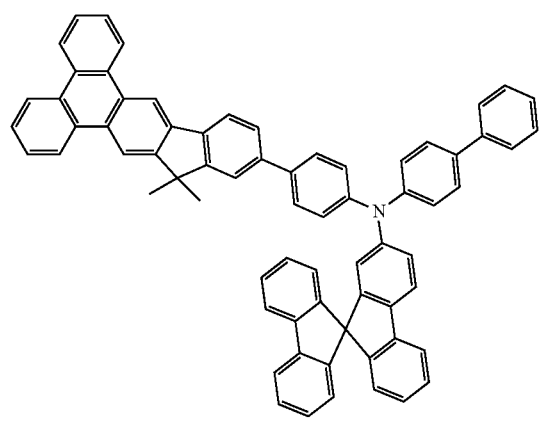
A28
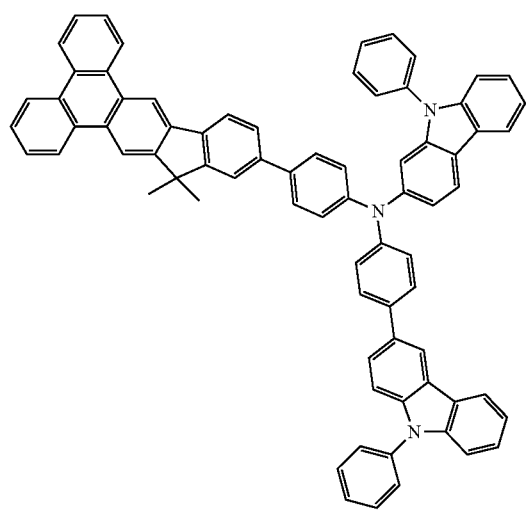
A29

-continued

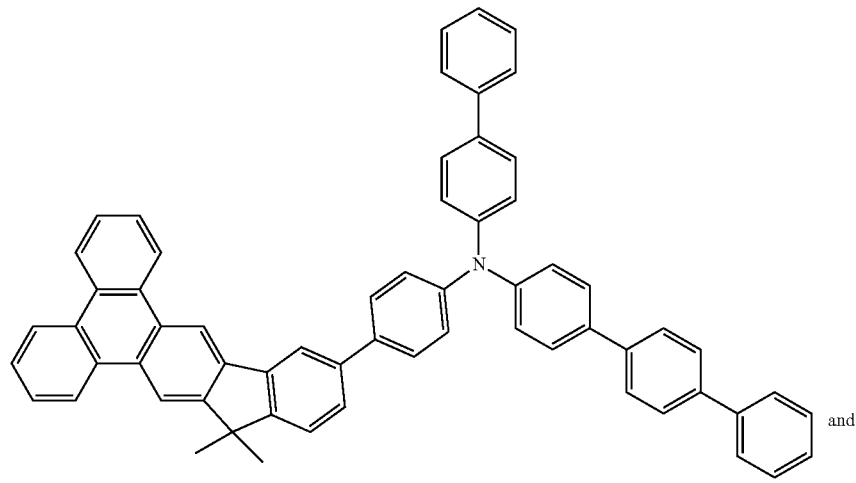

A30 and

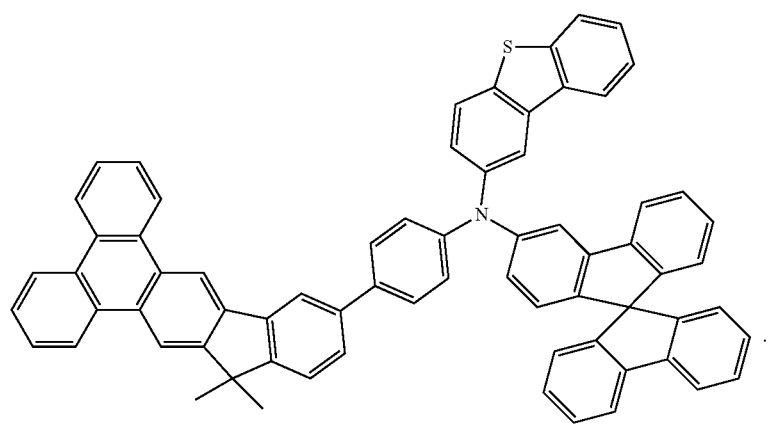

A31

5. An organic electroluminescent device comprising a pair of electrodes consisting of a cathode and an anode and between the pairs of electrodes comprising at least a layer of the indenotriphenylene-based amine derivative with a general formula (A) according to claim 1.

6. The organic electroluminescent device according to claim 5, wherein the layer of the indenotriphenylene-based amine derivative with a general formula (A) is a hole transport layer.

7. The organic electroluminescent device according to claim 5, wherein the layer of the indenotriphenylene-based amine derivative with a general formula (A) is an electron blocking layer.

* * * * *